(12) United States Patent
Abe et al.

(10) Patent No.: US 8,565,504 B2
(45) Date of Patent: Oct. 22, 2013

(54) ULTRASONIC IMAGE PROCESSING APPARATUS AND ULTRASONIC IMAGE PROCESSING METHOD

(75) Inventors: Yasuhiko Abe, Otawara (JP); Tetsuya Kawagishi, Nasushiobara (JP)

(73) Assignees: Kabushiki Kaisha Toshiba, Tokyo (JP); Toshiba Medical Systems Corporationq, Otawara-shi (JP)

( * ) Notice: Subject to any disclaimer, the term of this patent is extended or adjusted under 35 U.S.C. 154(b) by 1418 days.

(21) Appl. No.: 12/109,805

(22) Filed: Apr. 25, 2008

(65) Prior Publication Data
US 2008/0267482 A1    Oct. 30, 2008

(30) Foreign Application Priority Data
Apr. 26, 2007  (JP) ................................ 2007-117314

(51) Int. Cl.
*G06K 9/20* (2006.01)
*A61B 8/00* (2006.01)

(52) U.S. Cl.
USPC ............................ 382/131; 382/128; 600/437

(58) Field of Classification Search
USPC .......................... 382/128–131; 600/407–465; 324/300–322
See application file for complete search history.

(56) References Cited

U.S. PATENT DOCUMENTS

| | | | |
|---|---|---|---|
| 6,638,221 B2 | 10/2003 | Abe et al. | |
| 7,558,402 B2 * | 7/2009 | Zhou et al. | 382/103 |
| 2003/0083578 A1 * | 5/2003 | Abe et al. | 600/447 |
| 2005/0085729 A1 * | 4/2005 | Abe | 600/450 |
| 2007/0038087 A1 * | 2/2007 | Abe et al. | 600/437 |
| 2011/0190634 A1 * | 8/2011 | Kawagishi et al. | 600/443 |
| 2011/0301462 A1 * | 12/2011 | Hashimoto | 600/443 |

FOREIGN PATENT DOCUMENTS

| | | |
|---|---|---|
| JP | 2002-140690 | 5/2002 |
| JP | 2002-306483 | 10/2002 |
| JP | 2003-79620 | 3/2003 |
| JP | 2003-175041 | 6/2003 |
| JP | 2003-250804 | 9/2003 |
| JP | 2003-325519 | 11/2003 |
| JP | 2005-511129 | 4/2005 |
| JP | 2005-185333 | 7/2005 |

(Continued)

OTHER PUBLICATIONS

U.S. Appl. No. 12/540,135, filed Aug. 12, 2009, Ohuchi, et al.

(Continued)

*Primary Examiner* — Jermele M Hollington
*Assistant Examiner* — Emily Chan
(74) *Attorney, Agent, or Firm* — Oblon, Spivak, McClelland, Maier & Neustadt, L.L.P.

(57) ABSTRACT

Three slices, i.e., Basal, Mid, and Apical slices, which correspond to clinically useful ASE segmentation are designated, and the positions of the three slices are tracked through at least one cardiac cycle by performing three-dimensional speckle tracking in the remaining time phases. Three C-mode projection images concerning the tracked positions are reconstructed. In addition, arbitrary myocardial wall motion parameters at the tracked positions are computed and displayed upon being superimposed on C-mode images or projected/displayed on a polar map. As a C-mode projection image method, one of the following techniques can be used detecting and projecting only movement components perpendicular to slices determined in an initial time phase, detecting and projecting average movement components of the respective walls, and tracking and projecting each myocardial position. The obtained C-mode images are simultaneously displayed together with markers indicating the positions of long-axis images and C-mode images.

23 Claims, 19 Drawing Sheets

(56) References Cited

FOREIGN PATENT DOCUMENTS

| JP | 2006-314790 | 11/2006 |
| JP | 2007-44499 | 2/2007 |
| JP | 2008-515520 | 5/2008 |
| WO | WO 2006/038188 A2 | 4/2006 |
| WO | WO 2007/138751 A1 | 12/2007 |

OTHER PUBLICATIONS

U.S. Appl. No. 12/100,780, filed Apr. 10, 2008, Kazuno, et al.
U.S. Appl. No. 12/487,399, filed Jun. 18, 2009, Abe, et al.
U.S. Appl. No. 12/193,315, Aug. 18, 2008, Ohuchi, et al.
"iSlice View" QLAB's 3DQ Advanced plug-in features: Provide 9 equally-spaced MPR short axis views between the LV mitral annulus and apex (http://www.medical.philips.com/main/products/ultrasound/general/features/3dq_advanced/index.html) ( Not Avaliable).
Japanese Office Action issued Feb. 7, 2012, in Patent Application No. 2007-117314 (with English-language translation).
Japanese Office Action mailed Dec. 18, 2012 for Japanese Patent Application No. 2007-117314 (with English Translation).
Japanese Office Action for Patent Application No. 2012-088562, mailed Feb. 26, 2013 (with English translation).

* cited by examiner

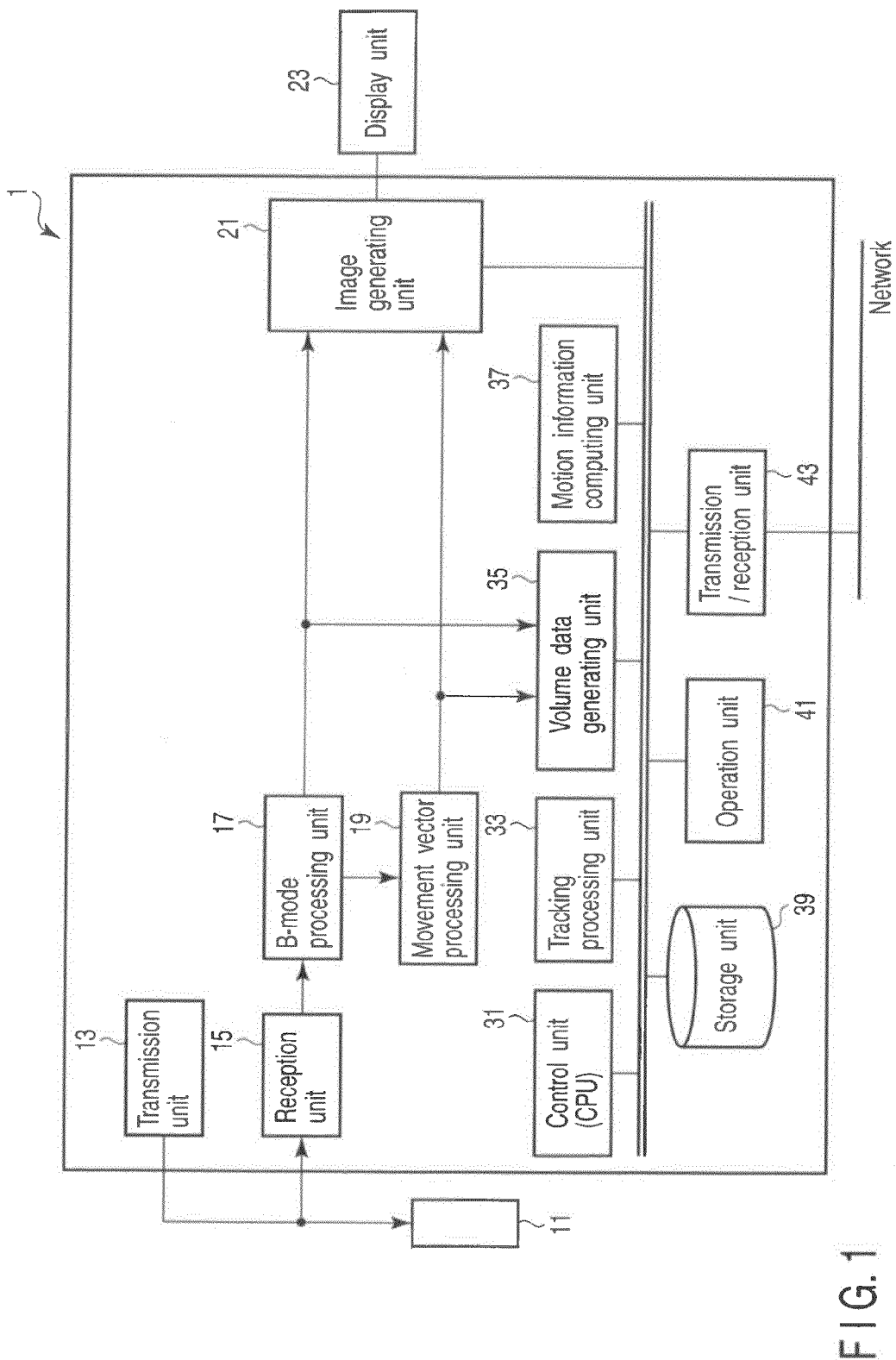
F I G. 1

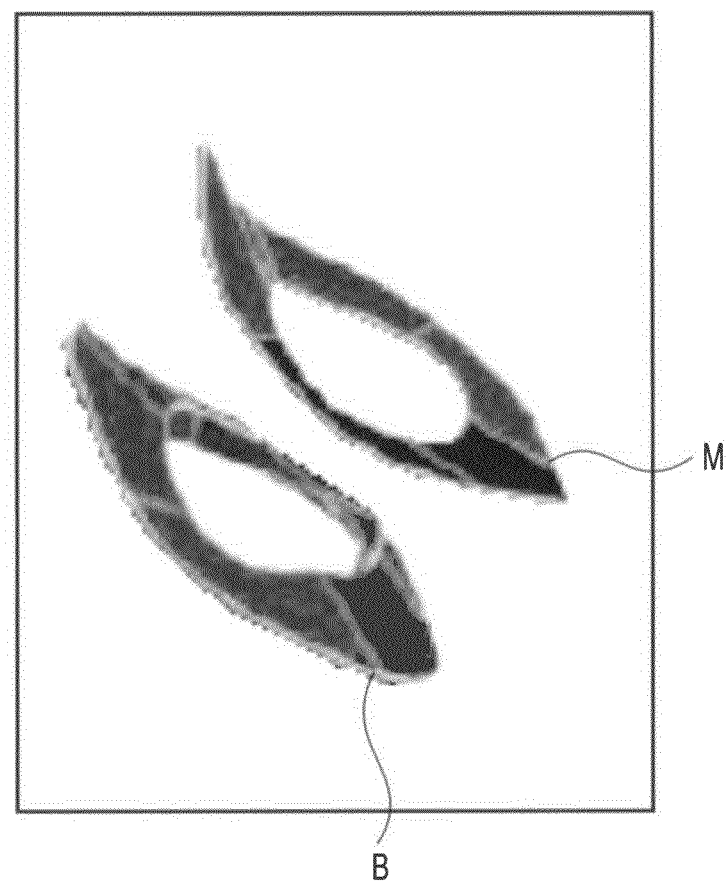
F I G. 10

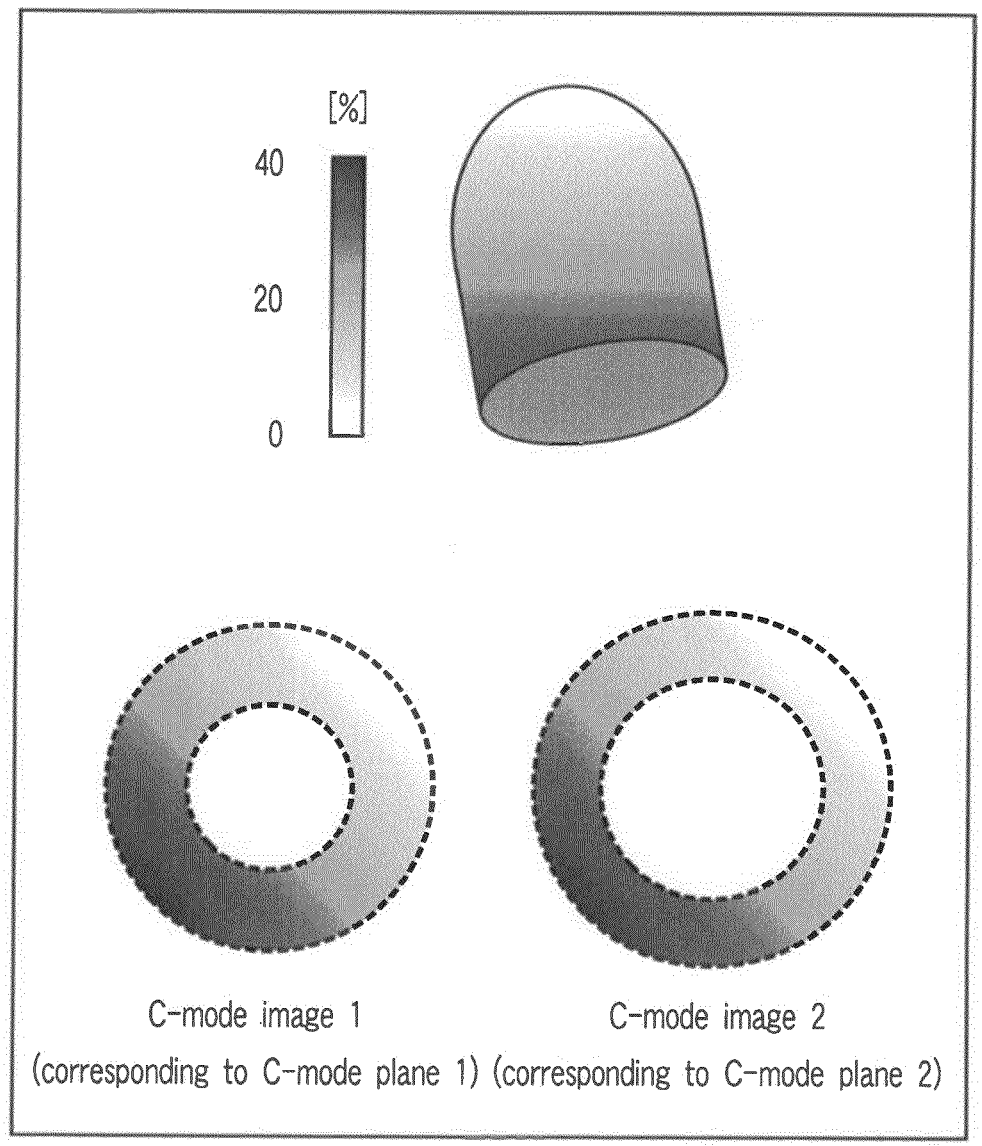
F I G. 21

ULTRASONIC IMAGE PROCESSING APPARATUS AND ULTRASONIC IMAGE PROCESSING METHOD

CROSS-REFERENCE TO RELATED APPLICATIONS

This application is based upon and claims the benefit of priority from prior Japanese Patent Application No. 2007-117314, filed Apr. 26, 2007, the entire contents of which are incorporated herein by reference.

BACKGROUND OF THE INVENTION

1. Field of the Invention

The present invention relates to an ultrasonic image processing apparatus and the like which can dynamically track a target locomotive tissue by using, for example, MPR images typified by C-mode tomograms in accordance with the motion of the tissue, and display, in a predetermined form, the motion information of the tissue computed by using the tracking result.

2. Description of the Related Art

An ultrasonic diagnosis technique can display, in real time, how a heart beats or a fetus moves, with simple operation of bringing an ultrasonic probe into contact with the body surface. In addition, this technique offers a high level of safety, and hence can be repeatedly used for examination. Furthermore, the system size is smaller than those of other diagnosis apparatuses such as X-ray, CT, and MRI apparatuses. Therefore, this apparatus allows easy examination upon being moved to a bed side. That is, the apparatus is a convenient diagnosis technique. Ultrasonic diagnosis apparatuses used in such ultrasonic diagnosis vary depending on the types of functions which they have. Some of compact apparatuses which can be carried with one hand have been developed. Ultrasonic diagnosis is free from the influence of radiation exposure such as X-ray exposure, and hence can be used in obstetric treatment, treatment at home, and the like.

It is very important for tissue diagnosis to objectively and quantitatively evaluate the function of a living tissue such as myocardial by using such an ultrasonic diagnosis apparatus. For example, as disclosed in Jpn. Pat. Appln. KOKAI Publication No. 2003-175041, there has recently been available, as a quantitative evaluation method for the heart, a technique of calculating local myocardial wall motion information such as displacement or strain while performing local pattern matching in images. Likewise, as disclosed in Jpn. Pat. Appln. KOKAI Publication No. 2003-175041, there is available a technique of accurately computing the three-dimensional distribution of myocardial wall motion information by using an ultrasonic diagnosis apparatus capable of acquiring three-dimensional images. These techniques can acquire three-dimensional myocardial wall motion information and quantitatively evaluate the function of a tissue.

In addition, there has recently been developed a technique of more specifically analyzing acquired three-dimensional motion information and displaying the resultant information in a predetermined form. For example, there is available a technique of calculating local myocardial wall motion information with respect to an arbitrary slice (MPR) image of dimensional data. In addition, as disclosed in Philips "iSlice View" QLAB's 3DQ Advanced plug-in features: Provides 9 equally-spaced MPR short axis views between the LV mitral annulus and apex (http://www.medical.philips.com/main/products/ultrasoud/general/qlab/features/3dq_advanced/index.html), a technique of acquiring transverse slice (C-mode) images of a left ventricle at a plurality of positions (e.g., nine positions) and displaying them side by side has been put into practice.

The following problems arise in the conventional method of analyzing three-dimensional motion information.

A conventional apparatus analyzes three-dimensional motion information by using MPR images at a temporally constant position (e.g., a plane whose position does not change with time). On the other hand, the myocardial generally moves while deforming in a complex manner. For this reason, the conventional technique cannot implement chronological observation of locally the same region (tissue). For example, the heart shortens in the long axis direction. If a constant slice is continuously observed by the conventional technique using C-mode images as short-axis images, pieces of different information in the long axis direction are sequentially replaced with each other with time.

In addition, the conventional apparatus displays nine C-mode images to cover an entire three-dimensional area as an observation target. As a result, the number of images to be observed becomes large, and hence it is difficult for an observer to simultaneously grasp all images. Furthermore, since a display range is generally limited, the display size per image decreases. This makes it difficult to observe a fine abnormal region.

BRIEF SUMMARY OF THE INVENTION

The present invention has been made in consideration of the above situation, and has as its object to provide an ultrasonic image processing apparatus and ultrasonic image processing method which can accurately and quickly acquire three-dimensional motion information concerning the same region of a moving diagnosis target.

According to an aspect of the present invention, there is provided an ultrasonic image processing apparatus comprising a storage unit which stores volume data acquired for each time phase concerning periodic motion of an object to be examined which periodically moves by scanning the object with ultrasonic waves, a setting unit which sets an arbitrary slice in volume data corresponding to a predetermined time phase, a tracking unit which sets a plane corresponding to the arbitrary slice in said each volume data corresponding to remaining time phases concerning the periodic motion by executing tracking processing of tracking a temporal change in a position of the arbitrary slice in the predetermined time phase, an image generating unit which generates a first ultrasonic image in said each time phase on the basis of data corresponding to the plane corresponding to the arbitrary slice in said each time phase, a display unit which displays the first ultrasonic image for each time phase.

According to another aspect of the present invention, there is provided an ultrasonic image processing apparatus comprising a storage unit which stores volume data acquired in each time phase of a heart by scanning the heart with ultrasonic waves, a computing unit which computes local movement information of the heart in each time phase by using the volume data, a setting unit which sets an arbitrary slice in volume data, an image generating unit which generates a first ultrasonic image in each time phase on the basis of tissue structure data corresponding to the arbitrary slice and a second ultrasonic image in each time phase by projecting the local movement information of the heart on the first ultrasonic image, and a display unit which displays the second ultrasonic image in each time phase.

According to yet another aspect of the present invention, there is provided an ultrasonic image processing method comprising setting an arbitrary slice in volume data corresponding to a predetermined time phase, the volume data being acquired for each time phase concerning periodic motion of an object to be examined which periodically moves by scanning the object with ultrasonic waves, setting a plane corresponding to the arbitrary slice in said each volume data corresponding to remaining time phases concerning the periodic motion by executing tracking processing of tracking a temporal change in a position of the arbitrary slice in the predetermined time phase, generating a first ultrasonic image in said each time phase on the basis of data corresponding to the plane corresponding to the arbitrary slice in said each time phase, displaying the first ultrasonic image for each time phase.

According to yet another aspect of the present invention, there is provided an ultrasonic image processing method comprising computing local movement information of the heart in each time phase by using the volume data acquired in each time phase of a heart by scanning the heart with ultrasonic waves, setting an arbitrary slice in volume data, generating a first ultrasonic image in each time phase on the basis of tissue structure data corresponding to the arbitrary slice and a second ultrasonic image in each time phase by projecting the local movement information of the heart on the first ultrasonic image, displaying the second ultrasonic image in each time phase.

BRIEF DESCRIPTION OF THE SEVERAL VIEWS OF THE DRAWING

FIG. 1 is a block diagram for explaining the arrangement of an ultrasonic diagnosis apparatus according to the first embodiment;

FIG. 10 is a view showing an example of a tracking method according to Example 3 in which the motion information obtained by tracking processing according to the first embodiment is displayed by three-dimensional surface rendering;

FIG. 21 is a view showing another example of the display form of a superimposed image obtained by projecting myocardial wall motion information in the wall thickness direction on a C-mode image.

DETAILED DESCRIPTION OF THE INVENTION

Figure 2:
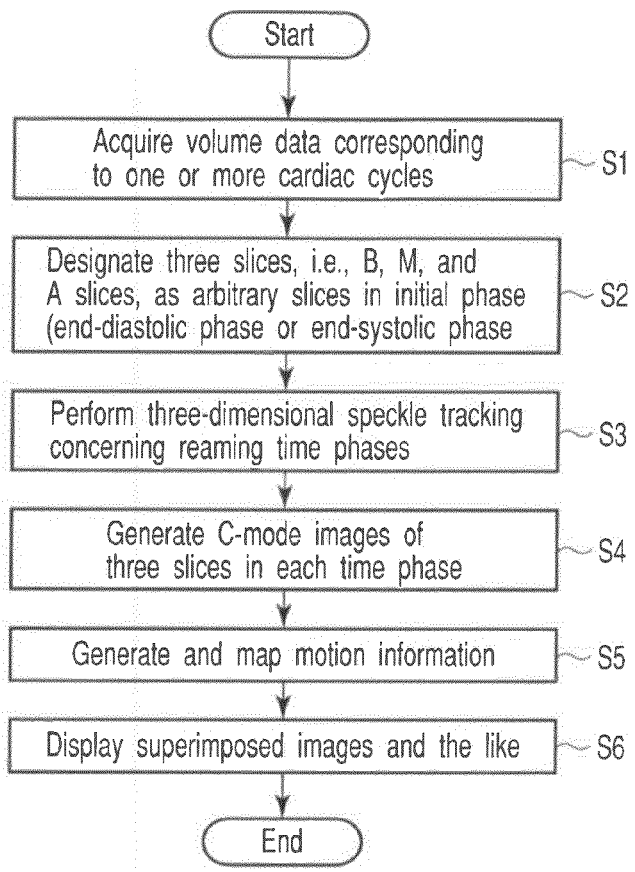
FIG. 2 is a flowchart showing a sequence of processing (arbitrary slice tracking processing) based on an arbitrary slice tracking function according to the first embodiment.

The first to third embodiments of the present invention will be described below with reference to the views of the accompanying drawing. Note that the same reference numerals denote constituent elements having substantially the same functions and arrangements in the following description, and a repetitive description will be made only when required.

First Embodiment

FIG. 1 is a block diagram showing the arrangement of an ultrasonic diagnosis apparatus 1 according to the first embodiment. The ultrasonic diagnosis apparatus 1 comprises an ultrasonic probe 11, a transmission unit 13, a reception unit 15, a B-mode processing unit 17, a movement vector processing unit 19, an image generating unit 21, a display unit 23, a control unit (CPU) 31, a tracking processing unit 33, a volume data generating unit 35, a motion information computing unit 37, a storage unit 39, an operation unit 41, and a transmission/reception unit 43. Note that when the present invention is applied to an ultrasonic image processing apparatus, the constituent elements of the apparatus are those enclosed by the dotted line in FIG. 1.

The ultrasonic probe 11 includes a plurality of piezoelectric transducers which generate ultrasonic waves on the basis of driving signals from the transmission unit 12 and convert reflected waves from an object to be examined into electrical signals, a matching layer provided for the piezoelectric transducers, a backing member which prevents ultrasonic waves from propagating backward from the piezoelectric transducers, and the like. When an ultrasonic wave is transmitted from the ultrasonic probe 11 to the object, various harmonic components are generated due to the nonlinearity of a living tissue upon propagation of ultrasonic waves. Fundamental waves and harmonic components constituting transmission ultrasonic waves are scattered backward by acoustic impedance boundaries of a tissue in a living body, micro-scattering, and the like, and are received as reflected waves (echoes) by the ultrasonic probe 11.

The transmission unit 13 includes a delay circuit, a pulser circuit, and the like (none are shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 12 applies a driving pulse to each transducer so as to form an ultrasonic beam toward a predetermined scanning line at the timing based on this rate pulse.

The reception unit 15 includes an amplifier circuit, an A/D converter, an adder, and the like (none are shown). The amplifier circuit amplifies an echo signal received via the probe 11 for each channel. The A/D converter gives the amplified echo signals delay times necessary to determine reception directivities. The adder then performs addition processing for the signals. With this addition, an ultrasonic echo signal corresponding to a predetermined scanning line is generated.

The B-mode processing unit 17 performs envelope detection processing for the ultrasonic echo signal received from the reception unit 15 to generate a B-mode signal corresponding to the amplitude intensity of the ultrasonic echo.

The movement vector processing unit 19 detects a tissue position by using pattern matching processing between two frames with different time phases and obtains the moving amount (or the velocity) of each tissue based on this moving position. More specifically, with regard to an area of interest on one frame, a corresponding area on the other frame which exhibits the highest similarity is obtained. The distance between the area of interest and the corresponding area allows to obtain the moving amount of the tissue. In addition, dividing this moving amount by the time difference between the frames makes it possible to obtain the moving velocity of the tissue. Performing this processing frame by frame at each position on each frame can acquire the spatiotemporal distribution data concerning the displacement (movement vector) of each local tissue.

The image generating unit 21 generates a B-mode ultrasonic image representing a dimensional distribution associated with a predetermined slice of a B-mode signal. The image generating unit 21 generates a B-mode ultrasonic image, an image associated with the motion information of a tissue, and a superimposed image including the B-mode ultrasonic image and the image associated with the motion information of the tissue. In this case, the motion information of the tissue is physical information which can be acquired concerning the motion of the tissue, e.g., the strain, strain rate, displacement, and velocity of the tissue. An image including such motion information of a tissue will be generically referred to as a "motion information image" hereinafter.

The display unit 23 displays morphological information in a living body, motion information, or the like as an image in a predetermined form on the basis of a video signal from the image generating unit 21. The display unit 23 displays markers for supporting positional association between images when a plurality of image are to be displayed.

The control unit (CPU) 31 has a function of an information processing apparatus (computer), and statically or dynamically controls this ultrasonic diagnosis apparatus. The control unit 31, in particular, implements an arbitrary slice tracking function (to be described later) by retrieving a dedicated program stored in the storage unit 39 in a memory (not shown).

The tracking processing unit 33 executes arbitrary slice tracking processing of chronologically tracking the movement of an arbitrary slice set in the volume data of a predetermined time phase.

The volume data generating unit 35 executes spatial interpolation processing by using B-mode data for each frame, which is received from the B-mode processing unit 17, spatial distribution data of tissue displacement for each time phase, which is received from the movement vector processing unit 19, and generates volume data concerning a diagnosis target which periodically moves for each time phase. Note that in this embodiment, the volume data generating unit 35 generates volume data by using data (so-called raw data) before the image generating unit 21. However, the present invention is not limited to this. It suffices to generate volume data by using data (so-called image data) from a unit after the image generating unit 21 in the volume data generating unit 35 and implement a slice tracking function (to be described later).

The motion information computing unit 37 computes motion information concerning each tracking target surface by using volume data concerning tissue displacement for each time phase, which is generated by the volume data generating unit 35, and a tracking target surface for each time phase, which is acquired by the tracking processing unit 33.

The storage unit 39 comprises a recording medium such as a magnetic disk (a floppy (registered trademark) disk, a hard disk, or the like), an optical disk (a CD-ROM or a DVD), or a semiconductor memory, and a device which reads out information recorded on the recording medium. The storage unit 39 stores transmission/reception conditions, a predetermined scanning sequence, raw data or ultrasonic image data (e.g., tissue image data captured in the tissue Doppler mode or the B mode) corresponding to each time phase, volume data for each time phase which is generated by the volume data generating unit 35, motion information generated by the motion information computing unit 37, a dedicated program for implementing the slice tracking function, a control program for executing image generation and display processing, diagnosis information (a patient ID, findings by a doctor, and the like), a diagnosis protocol, a body mark generation program, and the like.

The operation unit 41 is connected to the apparatus body and includes a mouse or a trackball, mode switches, a keyboard, and the like which are used to input, to the apparatus body, various instructions from the operator, an instruction to set a region of interest (ROI), various image quality setting instructions, the designation of an initial time phase in arbitrary slice tracking processing, the setting of an arbitrary slice in the initial time phase, and the like.

The transmission/reception unit 43 is a device which transmits/receives information to/from another apparatus via a network. Data, e.g., ultrasonic image data, the analysis result, and the like obtained by the ultrasonic diagnosis apparatus 1 can be transferred to another apparatus by the transmission/reception unit 43 via a network.

(Arbitrary Slice Tracking Function)

The arbitrary slice tracking function which the ultrasonic diagnosis apparatus 1 has will be described next. This function performs ultrasonic imaging to chronologically track spatial variations in arbitrary slices set in a diagnosis target exhibiting periodic motion, thereby supporting image diagnosis concerning the diagnosis target. For a concrete description, this embodiment exemplifies a case in which a diagnosis target exhibiting periodic motion is a heart.

FIG. 2 is a flowchart showing a sequence of processing (arbitrary slice tracking processing) based on the arbitrary slice tracking function according to the first embodiment. The contents of processing in each step will be described below.

[Step S1: Acquisition of Volume Data]

Volume scanning is executed on a heart as a diagnosis target throughout a period T to acquire the volume data of a B-mode signal and volume data concerning a tissue displacement in each of cardiac phases $t_0, t_1, \ldots, t_n$ (step S1).

Assume that the period T is a period corresponding to one or more cycles of motion of the diagnosis target (one or more cardiac cycles in this case). The volume scanning method to be used is not specifically limited. For example, it suffices to perform volume scanning by using either a one-dimensional array probe or a two-dimensional array probe. Alternatively, it suffices to use a three-dimensional triggered scanning technique of generating full volume data concerning a desired range by concatenating sub-volume data concerning small areas, acquired in synchronism with ECG, on the basis of associated triggers, and sequentially updating sub-volumes in accordance with time information.

[Step S2: Setting of Arbitrary Slices]

Arbitrary slices are set for volume data concerning any one of predetermined time phases (step S2). In this embodiment, three slices, namely, Basal, Mid, and Apical slices (to be referred to as B, M, and A surfaces, respectively, hereinafter for the sake of simplicity) are set in the initial time phase t0 in the period T.

It suffices to make the apparatus automatically set arbitrary slices for the volume data of the initial time phase or to manually set such slices in accordance with inputs from the operator using the operation unit 41. From a medical point of view, it is preferable that an initial time phase is an end-diastolic phase or an end-systolic phase.

[Step S3: Arbitrary Slice Tracking Processing]

The tracking processing unit 33 tracks each arbitrary slice by performing speckle tracking (tracking using a pattern matching technique) of an area corresponding to each arbitrary slice set in the initial time phase t0 in volume data of the remaining time phases (i.e., the time phases other than the initial time phase t0 in the period T) in which no slice has been set in step S2 (step S3).

A concrete technique for this arbitrary slice tracking operation will be described below according to the following examples with reference to FIG. 4.

Example 1

The tracking method according to this example obtains a movement component V by projecting movement vectors at the respective positions of tissues existing on the respective slices in the normal direction and averaging the vectors, and tracking an arbitrary slice in each time phase by using the movement component.

Figure 4:
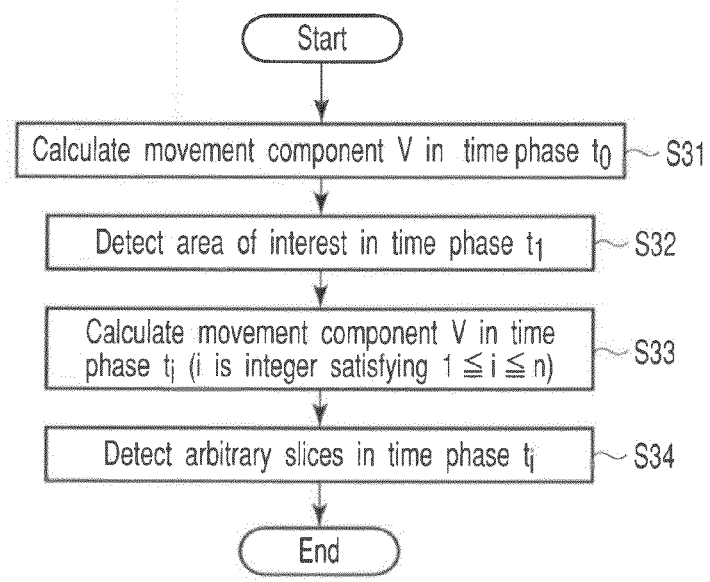
FIG. 4 is a flowchart showing a sequence of arbitrary slice tracking processing in step S3 in FIG. 2.
Figure 3:
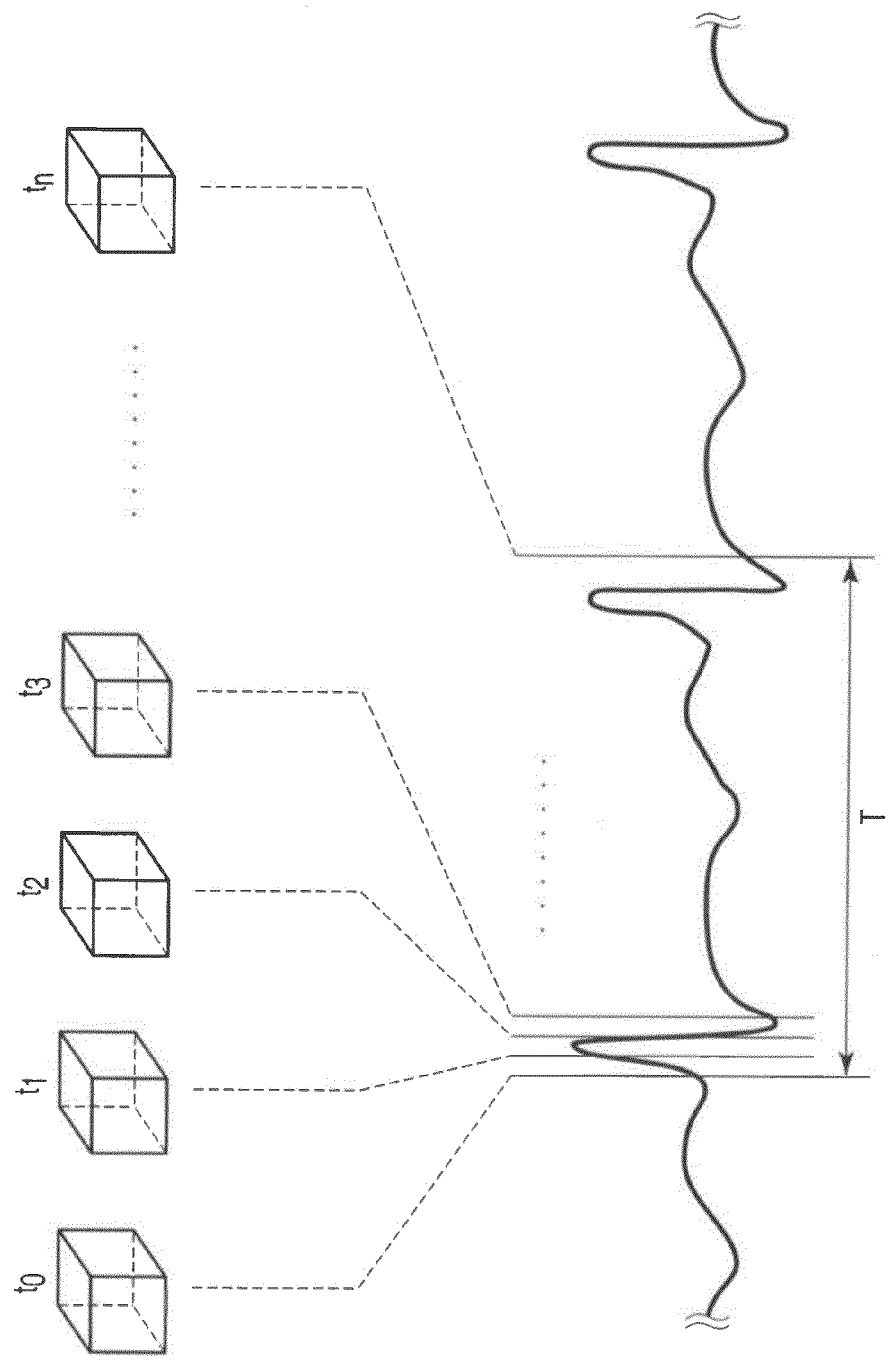
FIG. 3 is a view for explaining the acquisition of volume data concerning each cardiac phase in arbitrary slice tracking processing.

FIG. 4 is a flowchart showing a sequence of arbitrary slice tracking processing in step S3. As shown in FIG. 4, first of all, movement component $V=V_{z,mean}(t0)$ in the initial time phase t0 is calculated by averaging only normal-direction components (projection components in the normal direction shown by "z" in FIG. 4) of movement vectors of the respective tissues (i.e., the positions of tissues contained in the respective surfaces) on the B, M, and A surfaces set for the volume data of the initial time phase (step S31).

The B, M, and A surfaces set in the initial time phase are translated by movement component $V=V_{z,mean}(t0)$ along the normal direction, and cardiac areas contained in the B, M, and A surfaces after movement are set as arbitrary slices in a time phase t1 (step S32).

Movement component $V=V_{z,mean}(ti)$ in a time phase ti (i is an integer satisfying 2≤i≤n) is calculated by averaging only normal-direction components of movement vectors of the respective tissues on the B, M, and A surfaces in the time phase t1 (step S33).

The B, M, and A surfaces in the time phase ti are translated by movement component $V=V_{z,mean}(ti)$ along the normal direction to set the B, M, and A surfaces in the time phase ti (step S34).

Sequentially repeating the processing in steps S33 and S34 in chronological order up to the time phase tn can track the B, M, and A surfaces in the respective time phases.

Figure 5:
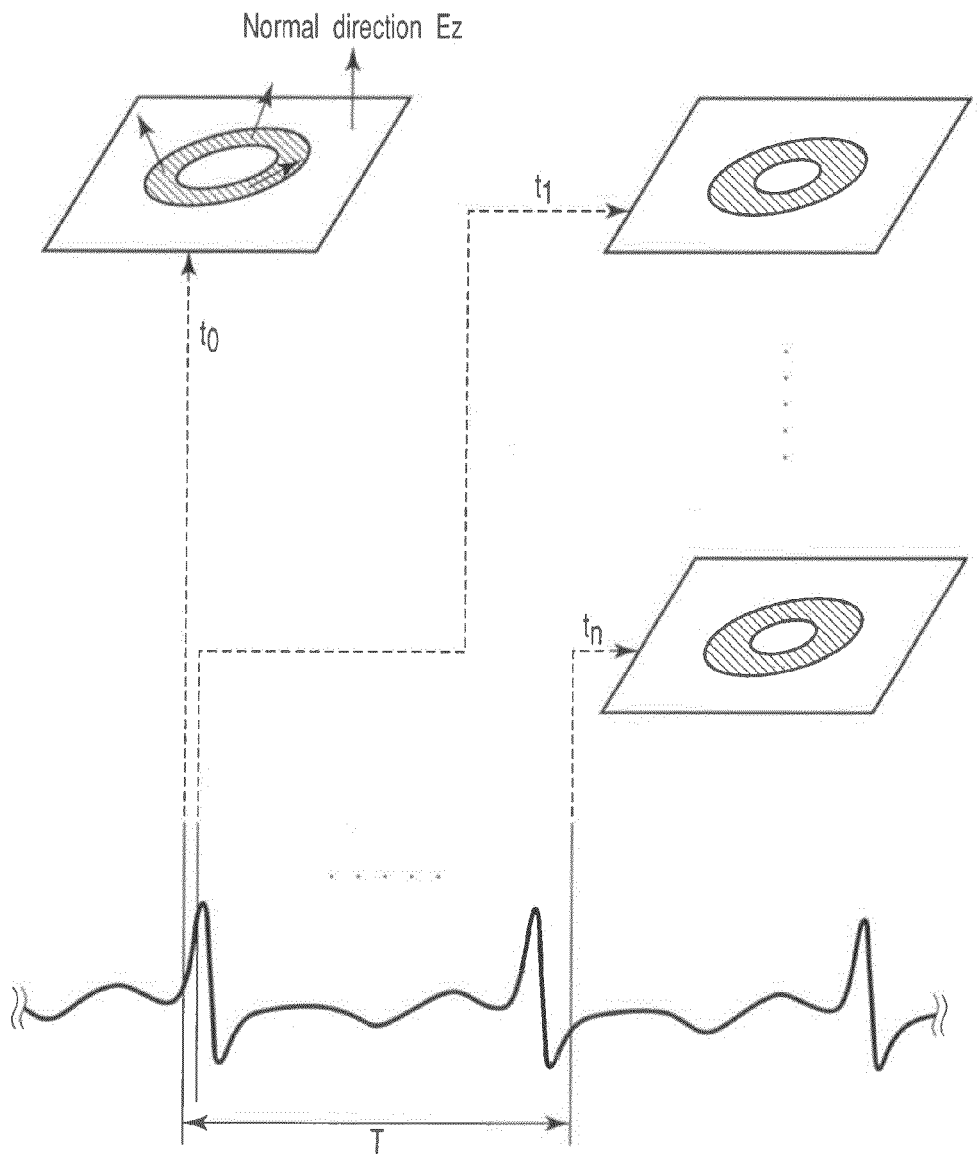
FIG. 5 is a view for explaining a tracking method according to Example 1.

The positions of the B, M, and A surfaces to be tracked by the above technique according to Example 1 after movement are detected by using the movement component V calculated by averaging only the normal-direction components at the respective positions (the respective myocardials) on the respective surfaces. Therefore, as shown in FIG. 5, the B, M, and A surfaces in the respective time phases are parallel to the B, M, and A surfaces set in the initial time phase.

Example 2

The tracking method according to this example obtains the movement component V by averaging movement vectors at the respective positions of tissues existing in set arbitrary slices (without projection in the normal direction) and tracks arbitrary slices in each time phase by using the obtained component.

Referring to FIG. 4, first of all, movement component $V=V_{mean}(t0)$ is calculated by averaging the movement vectors of the respective myocardials (i.e., the respective positions on tissues included in the respective surfaces) in the B, M, and A surfaces set for the volume data of the initial time phase (step S31).

The B, M, and A surfaces set in the initial time phase are translated by movement component $V=V_{mean}(t0)$ to set the B, M, and A surfaces in the time phase t1 (step S32).

Movement component $V=V_{mean}(ti)$ in the time phase ti (i is an integer satisfying 2≤i≤n) is calculated by averaging the movement vectors of the respective myocardials on the B, M, and A surfaces in the time phase t1 (step S33).

The B, M, and A surfaces in the time phase ti are translated by movement component $V=V_{mean}(ti)$ along the normal direction to set the B, M, and A surfaces in the time phase ti (step S34).

Sequentially repeating the processing in steps S33 and S34 in chronological order up to the time phase tn can track arbitrary slices in the respective time phases.

Figure 6:
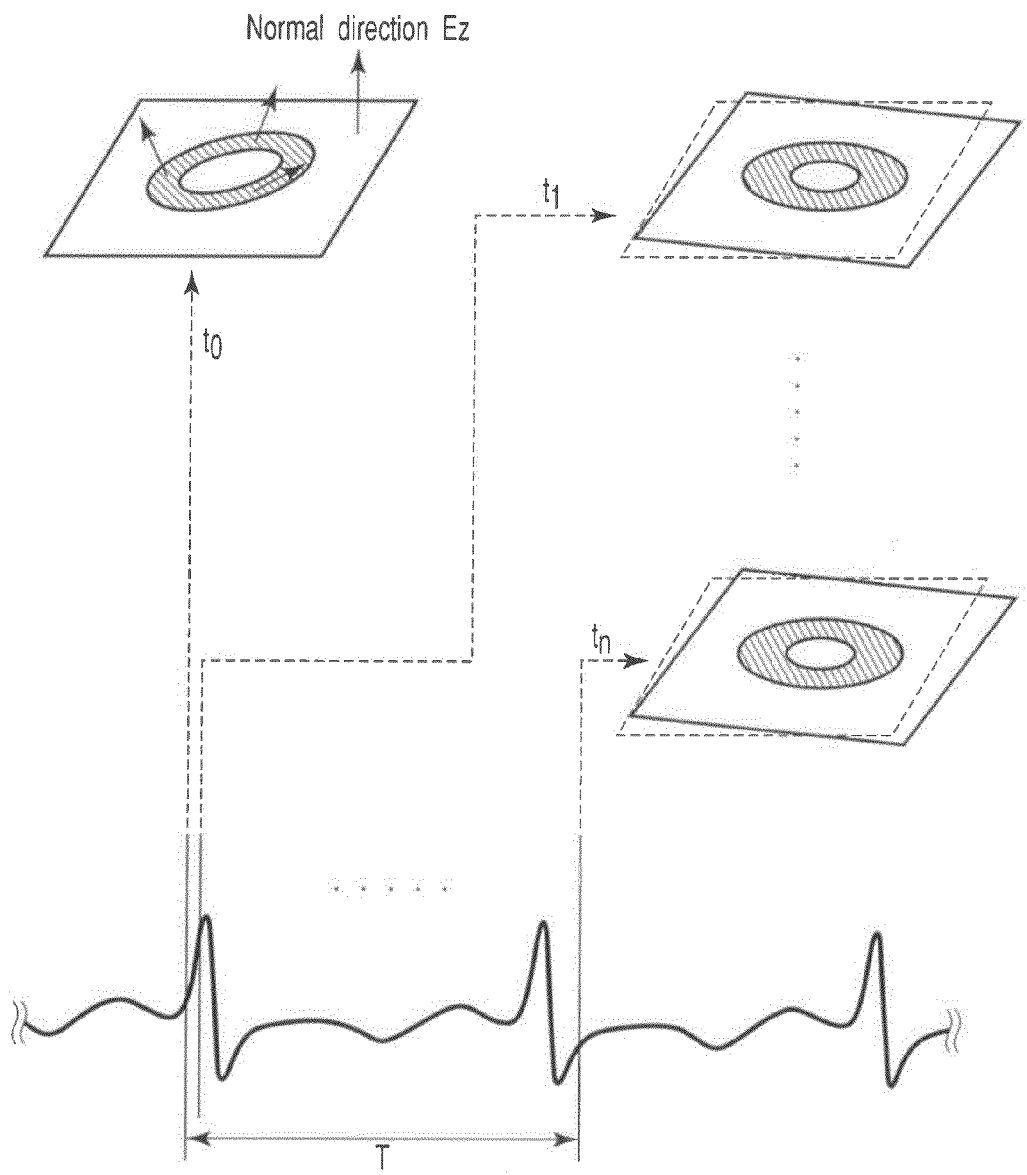
FIG. 6 is a view for explaining a tracking method according to Example 2.

The positions of the B, M, and A surfaces to be tracked by the technique according to Example 2 after movement are detected by using the movement component V calculated by averaging the movement vectors of the respective positions (the respective myocardials) on the respective surfaces. As shown in FIG. 6, therefore, the B, M, and A surfaces in the respective time phases are not always parallel to the B, M, and A surfaces set in the initial time phase.

Example 3

The tracking method according to this example detects the respective positions of tissues existing in set arbitrary slices in the next time phase by using movement vectors at the respective positions, and chronologically repeats the detection, thereby tracking arbitrary slices in each time phase.

That is, as shown in FIG. 4, first of all, this method calculates movement vector $V=V(j, t0)$ associated with each position pj(x, y, z) (j is an integer satisfying 1≤j≤m where m is the number of positions of myocardial tissues existing on the respective surfaces) on each of the B, M, and A surfaces set for the volume data of the initial time phase t0 (step S31).

The method then detects the respective positions on the B, M, and A surfaces in the initial time phase after they are moved by movement vector V=V(j, t0), and sets the resultant surfaces as the B, M, and A surfaces in the next time phase t1 (step S32).

The method calculates movement vector V=V(j, t1) at each position on each of the B, M, and A surfaces in the time phase t1 (step S33).

The method detects the respective positions on the B, M, and A surfaces in the time phase t1 after the respective positions on the B, M, and A surfaces are moved by movement vector V=V(j, t1), and sets the resultant surfaces as the B, M, and A surfaces in the next time phase ti (i is an integer satisfying 2≤i≤n) (step S34).

Chronologically repeating the processing in steps S33 and S34 up to the phase tn can track arbitrary slices in each time phase.

Figure 7:
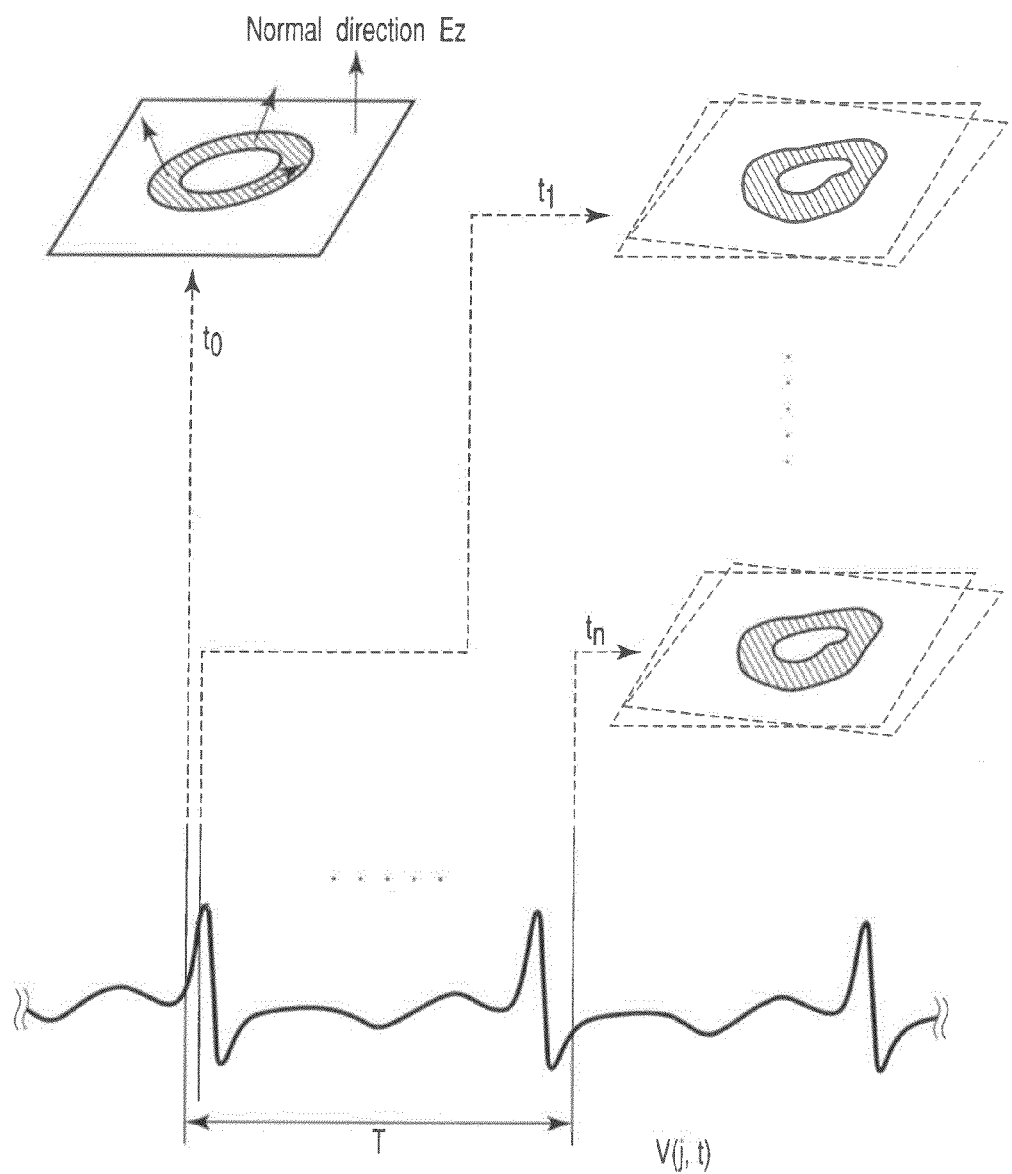
FIG. 7 is a view for explaining a tracking method according to Example 3.

The technique according to Example 3 detects positions constituting the B, M, and A surfaces in the next time phase by using movement vectors at the respective positions (the respective myocardials) on the B, M, and A surfaces to be tracked, and chronologically repeats the detection operation to track arbitrary slices in each time phase. As shown in FIG. 7, therefore, the B, M, and A surfaces in each time phase become arbitrary curved surfaces in a three-dimensional coordinate system in each time phase after the initial time phase.

Note that Examples 3, 2, and 1 allow the placement of accurate motion information corresponding to more local tracking positions in the order named.

[Step S4: Generation of C-Mode Image]

The image generating unit 21 projects data (arbitrary slice data) belonging to an arbitrary slice in each time phase on a projection surface to generate an ultrasonic image (C-mode image) (step S4). Consider the manner of projecting arbitrary slice data in each tracking method. When the tracking method according to Example 1 or 2 is used, a tracked arbitrary slice (a plane surface in either method) is preferably made to coincide with a projection surface in advance.

Figure 8:
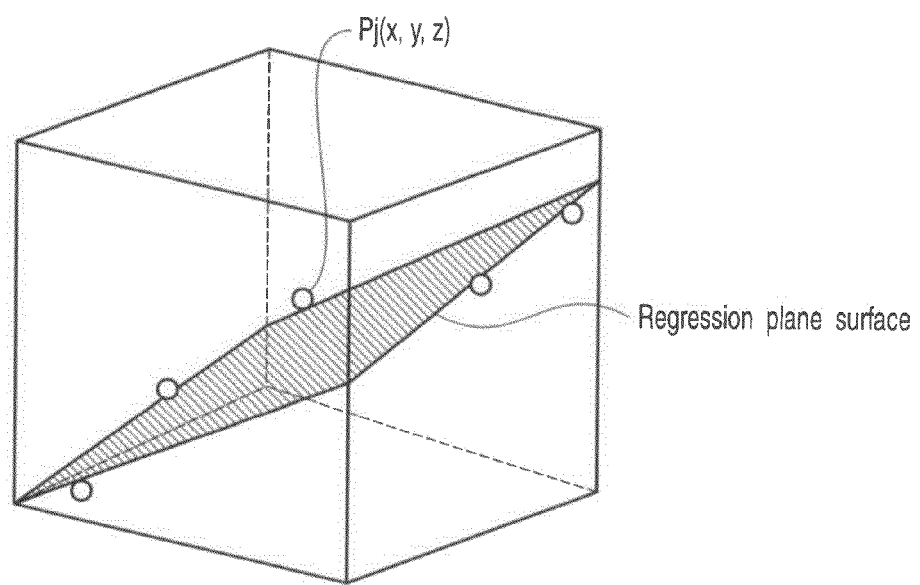
FIG. 8 is a view for explaining image reconstruction when the tracking method according to Example 3 is used.

When the technique according Example 3 is used, a tracked arbitrary slice does not always become a plane surface. As shown in FIG. 8, therefore, it is preferable to obtain a regression plane surface concerning each minute local position (each position pj(x, y, z) tracked in tracking processing) on myocardial within a tracked arbitrary slice and reconstruct an ultrasonic image (C-mode image) by using the regression plane surface as a projection surface. Alternatively, a C-mode image concerning a regression plane surface can be generated by directly using data at each position on the regression plane surface.

[Step S5: Computation of Motion Information]

The motion information computing unit 37 computes motion information concerning an arbitrary slice in each time phase (step S5). The motion information computation technique to be used is not specifically limited. Assume that this embodiment uses the tissue strain imaging method described in, for example, Jpn. Pat. Appln. KOKAI Publication No. 2003-175041.

Note that the tissue strain imaging method requires a velocity distribution image concerning a plurality of time phases. This velocity distribution image can be obtained by performing pattern matching processing for a plurality of two-dimensional or three-dimensional tissue images concerning a plurality of time phases which are acquired in the B mode or the like.

[Step S6: Image Display]

Motion information images concerning arbitrary slices tracked by arbitrary slice tracking processing are displayed (step S6). That is, the image generating unit 21 generates a motion information image by projecting motion information at each position in the arbitrary slice generated in step S5 onto the projection surface set in step S4. When the projection surface is a regression plane surface, motion information at each position on the regression plane surface is obtained and is superimposed on the C-mode image generated in step S4, thereby generating a motion information image. The display unit 23 continuously displays (tracking displays) the generated motion information images in time phase order.

When displaying motion information images, it is possible to display tomograms (long-axis images in this case) perpendicular to the motion information images simultaneously with the motion information images and also marker-display positions on the long-axis images which correspond to the motion information images.

Figure 9:
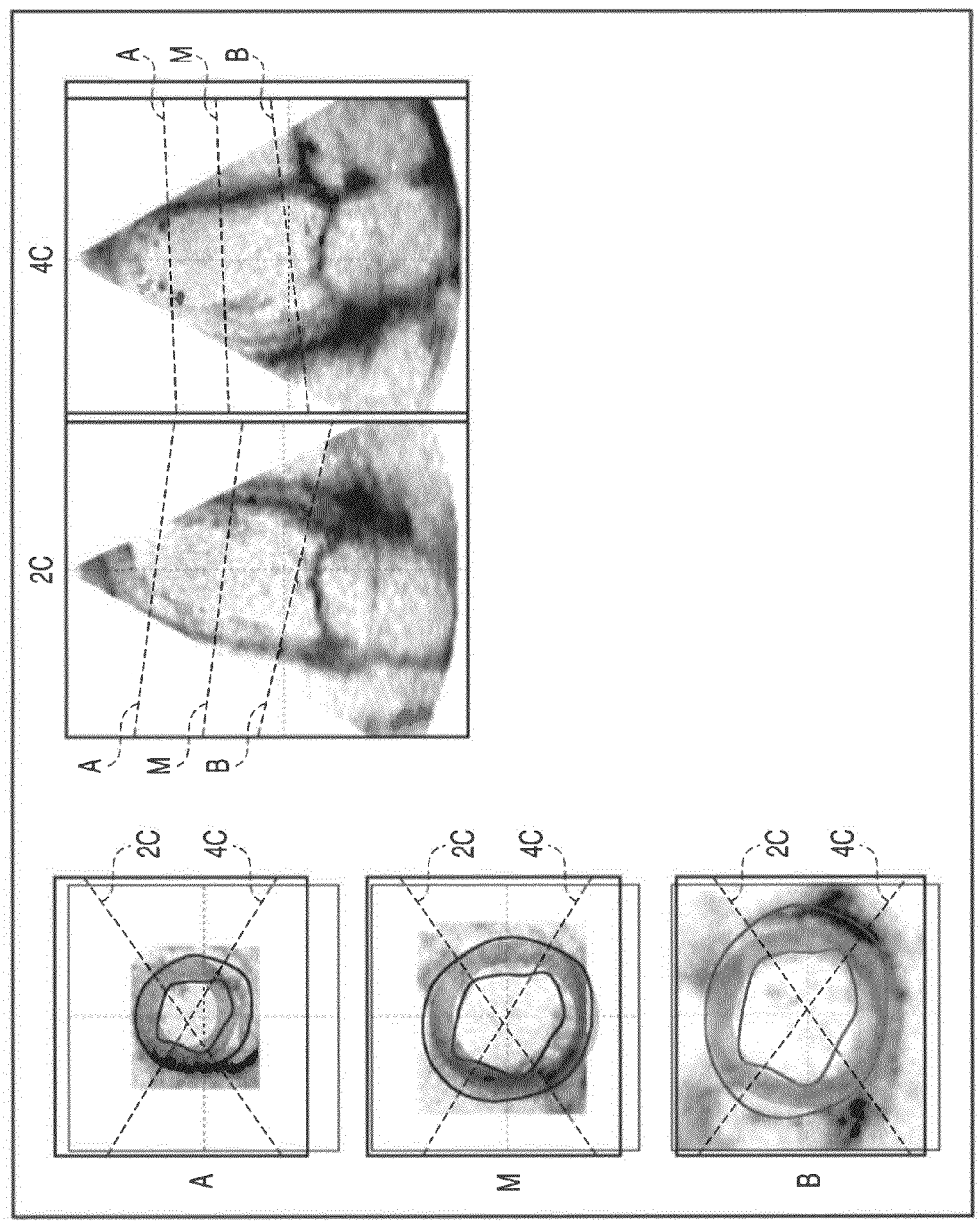
FIG. 9 is a view showing an example of the display form of motion information obtained by tracking processing according to the first embodiment.

FIG. 9 is a view showing an example of marker display of positions on long-axis images which correspond to motion information images. Referring to FIG. 9, the broken lines on the respective long-axis images, i.e., the 4C and 2C images, represent the marker display of positions on the motion information images which correspond to the B, M, and A surfaces. The broken lines on the respective motion information images (short-axis images), i.e., the B, M, and A surfaces, represent the marker display of positions corresponding to the 4C and 2C images, respectively.

Such marker display allows to grasp the positions of the B, M, and A surfaces which dynamically follow up with each other and to also grasp a region which exhibits a local reduction in shortening in the long-axis direction due to myocardial ischemia or the like. This state can be understood as follows. If, for example, on the long-axis image on the left side in FIG. 9, the positions of the three short-axis images corresponding to the B, M, and A surfaces are parallel, all the Basal, Mid, and Apical areas on the left and right cardiac walls uniformly move. In contrast, if only the short-axis image corresponding to the M surface slopes down to the left relative to the remaining slices, it indicates that the shortening of the Basal region of the left myocardial is locally smaller than that of the Basal region of the right myocardial.

In addition, it is possible to perform three-dimensional surface rendering display of motion information concerning tracked arbitrary slices.

FIG. 10 is a view showing an example of three-dimensional surface rendering display of motion information concerning tracked arbitrary slices. FIG. 10 shows how transverse slices of the myocardial deform while changing their positions. Different colors are assigned to the different degrees of a myocardial wall motion parameter (e.g., radial-strain).

(Effects)

According to the above arrangements, the following effects can be obtained.

This ultrasonic diagnosis apparatus calculates a movement vector in each time phase, and detects arbitrary slices in the next time phase by using the movement vector. The apparatus repeats this operation to track spatial variations in arbitrary slices. Using data on arbitrary slices in the respective time phases which are obtained by tracking makes it possible to generate C-mode images and motion information images and continuously display them in, for example, chronological order. Such display allows to intuitively and quantitatively grasp how the slices of the myocardial deform with time in accordance with cardiac phases. This makes it possible to accurately and quickly acquire three-dimensional motion information concerning the same region of the myocardial which moves.

Even with shortening, it is possible to always observe motion information, e.g., a change in the wall thickness of the myocardial in the same local segment. In addition, since only three C-mode images corresponding to three areas necessary for the clinical analysis of the entire left ventricle, which are recommended by ASE, are used, it is easy to simultaneously grasp the images as compared with observation using the conventional apparatus.

Second Embodiment

The second embodiment of the present invention will be described next. The first embodiment exemplifies a case in which cardiac areas contained in B, M, and A surfaces corresponding to short-axis images are tracked. Arbitrary slice tracking processing according to this embodiment is performed by using an apical four-chamber slice (4C slice), apical three-chamber slice (3C slice), and apical two-chamber slice (2C slice) corresponding to clinically significant long-axis images. A technique according to this embodiment can be executed independently of or in combination with the techniques described in the first embodiment.

More specifically, the following exemplifies a case in which arbitrary slices corresponding to long-axis images are 4C and 2C slices. However, the present invention is not limited to this. It suffices to use any combination of 4C, 3C, and 2C slices or use all the three slices or only one slice.

Figure 11:
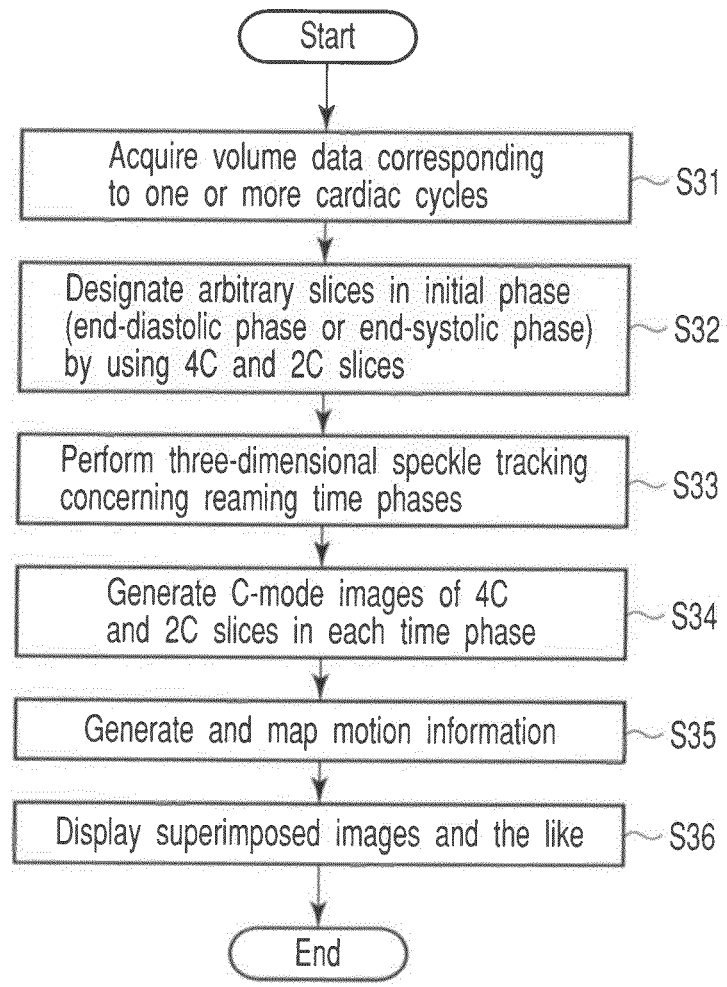
FIG. 11 is a flowchart showing a sequence of arbitrary slice tracking processing according to the second embodiment.

FIG. 11 is a flowchart showing a sequence of arbitrary slice tracking processing according to the second embodiment. The contents of processing in each step will be described below.

As shown in FIG. 11, as in the first embodiment, volume data of a heart as a diagnosis target concerning each of cardiac phases t0, t1, ..., tn is acquired by volume scanning throughout a period T (step S31). 4C and 2C slices are set as arbitrary slices with respect to the volume data concerning the initial time phase (step S32).

The tracking processing unit 33 executes arbitrary slice tracking by speckle tracking of areas corresponding to the 4C and 2C slices set in the initial time phase t0 in volume data of the remaining time phases (i.e., the time phases other than the initial time phase t0 in the period T) in which no slice has been set in step S32 (step S33). Obviously, it is possible to use the same arbitrary slice tracking method as that described in the same manner of first embodiment.

An image generating unit 21 then generates 4C and 2C images by projecting the tracked 4C and 2C slices in each time phase (step S34). A motion information computing unit 37 computes arbitrary motion information defined on the tracked 4C and 2C slices in each time phase. The display unit 23 displays the computed motion information as motion information images superimposed on the 4C and 2C images (steps S35 and S36).

Figure 12:
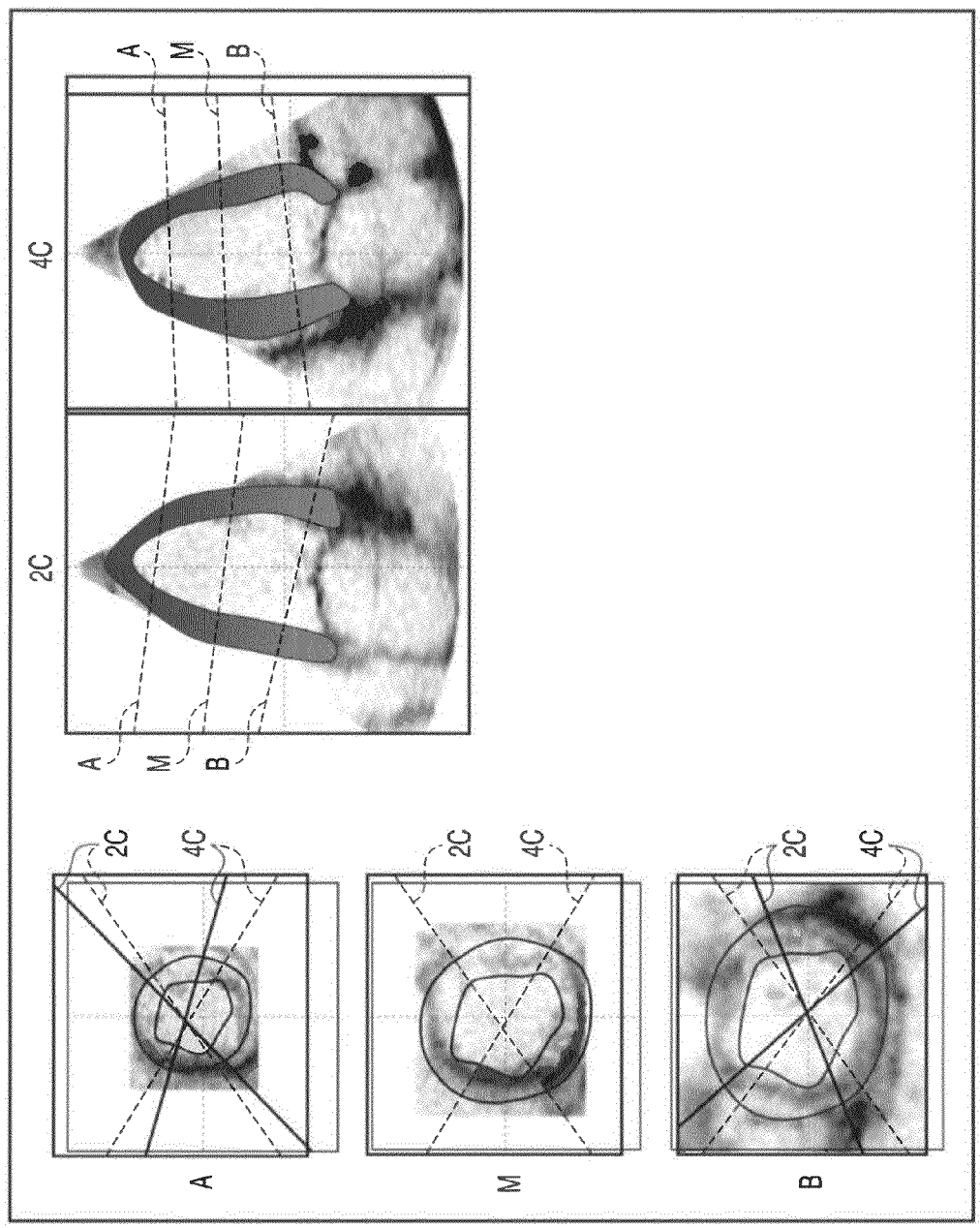
FIG. 12 is a view showing an example of the display form of motion information obtained by tracking processing according to the second embodiment.

At this time, as in, for example, the first embodiment, the motion information images are displayed such that positions in the respective short-axis images which correspond to long-axis images are marker-displayed simultaneously with a plurality of short-axis images, thereby supporting to grasp slice positions and tracking positions on the long-axis images. FIG. 12 shows a preferred display example (the cardiac phase of the motion information images is an end-systolic phase) in a case in which when such marker display is performed, projection is performed on regression plane surfaces obtained by the tracking method described in Example 3. The two broken-line markers displayed on the respective short-axis images respectively correspond to the positions of the 4C and 2C images in an end-diastolic phase, and the solid lines respectively indicate the markers of the respective long-axis images in an end-systolic phase. Such display allows to grasp the state and degree of the torsional motion of the myocardial wall when, for example, the long-axis image marker in the short-axis image at the Apical level rotates in the counter-clockwise direction, and the long-axis image marker in the short-axis image at the Basal level rotates in the clockwise direction which is reverse to that at the Apical level.

Figure 13:
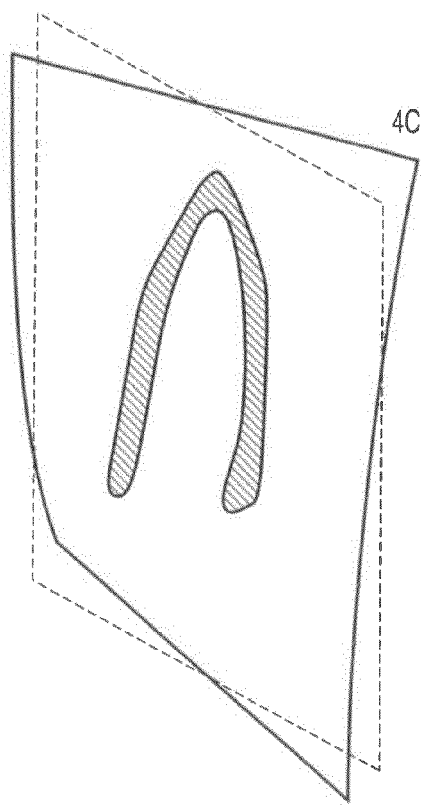
FIG. 13 is a view showing a case in which the motion information obtained by tracking processing according to the second embodiment is displayed by three-dimensional surface rendering.

According to the above display example, even a long-axis image after tracking is projected as a two-dimensional tomogram. However, in order to facilitate grasping how the shape of the long-axis image changes, it suffices to perform three-dimensional surface rendering display of the image, as shown in an example of the image of FIG. 13. According to the example shown in FIG. 13, the start of tracking is set at an end-diastolic time, and a long-axis image position at the end-diastolic time is guide-displayed with the broken line, while a long-axis image position after tracking at an end-systolic time is indicated by the solid line. Using such a display form facilitates grasping a torsional motion or the like when it occurs.

With the above arrangement, the same effects as those of the first embodiment can be obtained. It is generally known that the myocardial wall of a healthy left ventricle twists, as if a dust cloth were squeezed, to circulate blood through the entire body. Seeing the above long-axis image makes it possible to always observe motion information exemplifying a change in myocardial contraction rate of the myocardial in the same local segment in the long-axis direction.

Third Embodiment

The third embodiment of the present invention will be described next. The first and second embodiments obtain three-dimensional movement vectors to track arbitrary slices, and perform three-dimensional tracking by using the vectors. In contrast, the third embodiment exemplifies a case in which a similar effect can be easily obtained by using a two-dimensional tracking technique capable of performing computation faster than three-dimensional tracking.

Figure 14:
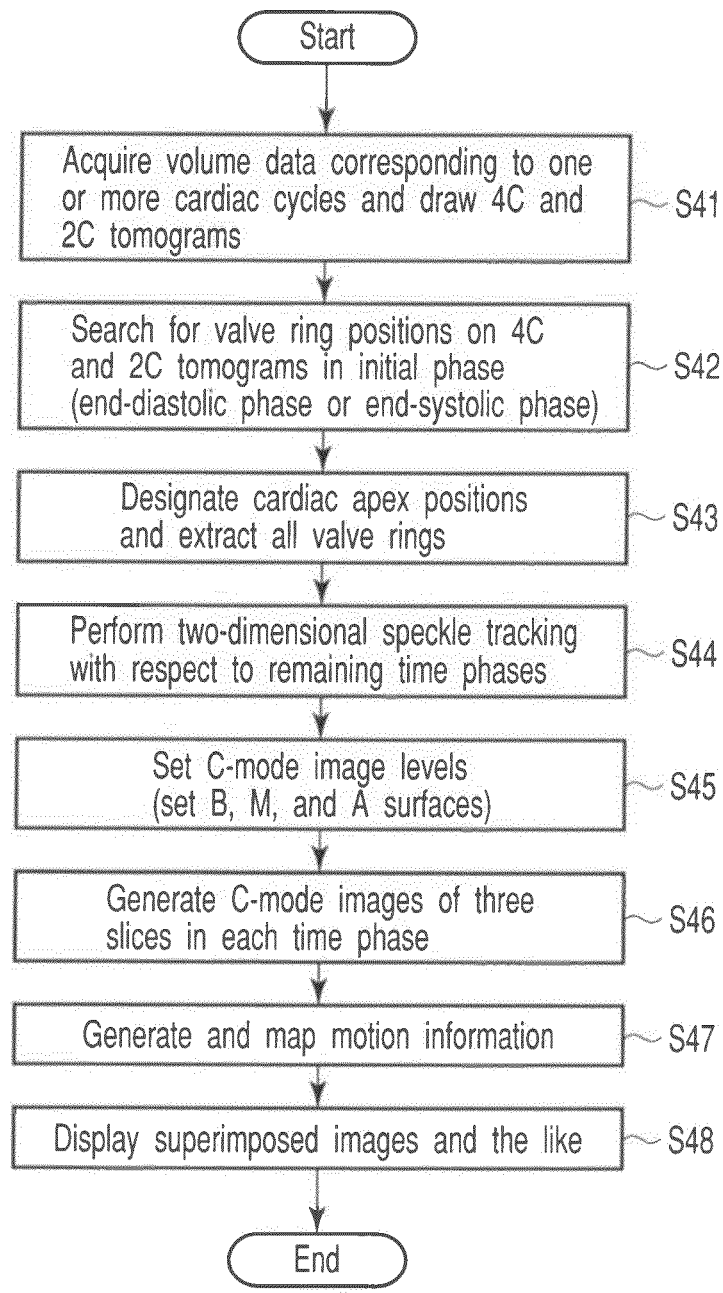
FIG. 14 is a flowchart showing a sequence of arbitrary slice tracking processing according to the third embodiment.

FIG. 14 is a flowchart showing a sequence of arbitrary slice tracking processing according to the third embodiment. The contents of processing in each step will be described below.

Referring to FIG. 14, first of all, volume data of a heart as a diagnosis target concerning each of cardiac phases t0, t1, ..., tn are obtained by volume scanning throughout a period T, and two long-axis slices comprising 4C and 2C images or three long-axis slices comprising 4C, 2C, and 3C images are rendered (step S41).

Upon receiving information indicating an initial time phase (preferably an end-diastolic phase or end-systolic phase) at which tracking designated by the operator on the basis of each rendered long-axis slice is started, a tracking processing unit 33 searches for left and right, two annulus positions per long-axis slice in the initial time phase by the two-dimensional pattern matching technique using a pre-registered annulushape dictionary as a template (step S42). Note that each annulus position can be manually designated in accordance with an input from the operator through an operation unit 41 instead of using the pattern matching technique.

When the position of a cardiac apex portion in each time phase is designated, the tracking processing unit 33 extracts all annulus in the initial time phase on the basis of the designated position of the cardiac apex portion and the two annulus positions found in step S42 (step S43). When the position of a cardiac apex portion in each time phase is to be designated, first of all, the position of a cardiac apex portion is designated on a long-axis tomogram in a predetermined time phase on the basis of the designation by the operator through the operation unit 41, and the designated position is shared in long-axis tomograms in the remaining time phases. However, the technique used for designating the position of a cardiac apex portion is not limited to this technique. For example, it suffices to individually designate the position of a cardiac apex portion on each of all long-axis tomograms by a predetermined method and designate the average position among all the long-axis tomograms as the position of a new cardiac apex portion. In general, the movement of a cardiac apex portion is small. For this reason, in such cardiac apex position designation, the setting result in a given time phase is preferably shared in all the remaining time phases.

All annulus positions are tracked in each long-axis image in at least one cardiac cycle by performing tracking operation using the two-dimensional pattern matching technique (step S44).

The tracking processing unit 33 then sets a C-mode image level (step S45). That is, the tracking processing unit 33 obtains the barycentric position of four or six annulus positions on a long-axis image in each time phase, and defines a central axis connecting the barycenter and the cardiac apex position in each time phase. The tracking processing unit 33 then divides the central axis into three portions, and designates the levels of short-axis slices (i.e., the levels of B, M, and A surfaces) in the respective areas. Most simply, the central position of each area on the central axis can be designated as the level of each short-axis slice. Since slices at the respective levels can be defined by defining the central axis as a normal vector, the defined slices are set as short-axis slices (B, M, and A surfaces).

C-mode images concerning the set short-axis slices are reconstructed (step S46). C-mode images are reconstructed in the above manner.

Figure 15:
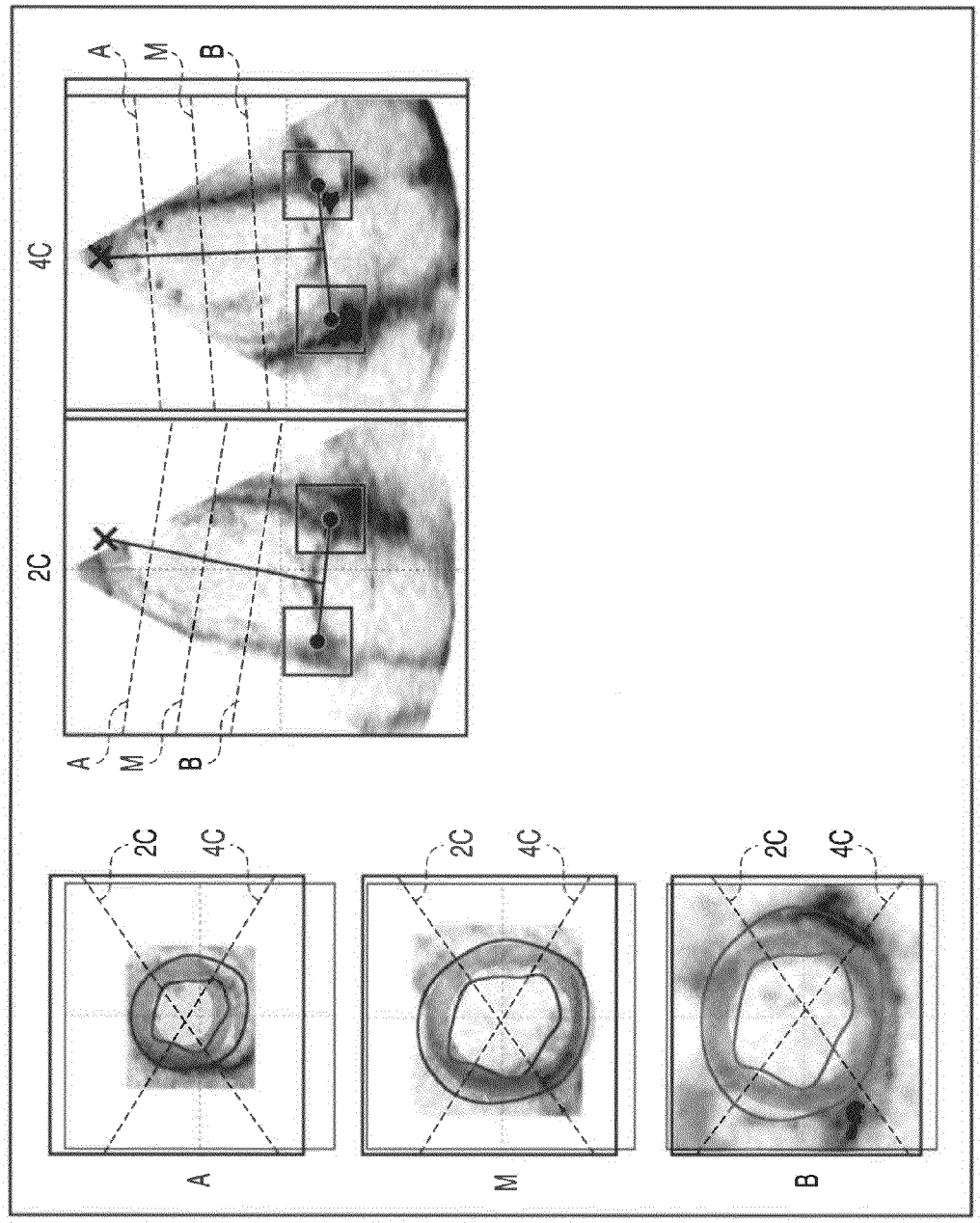
FIG. 15 is a view showing an example of the display form of motion information obtained by tracking processing according to the third embodiment.

Arbitrary myocardial wall motion parameters such as a radial-strain are computed by performing two-dimensional tracking in short-axis images tracked in the central axis direction in the above manner (step S47). The computed parameters are superimposed on the above C-mode images and displayed (step S48). FIG. 15 shows a preferred display example based on this embodiment.

According to the above arrangement, with regard to, for example, shortening, it is possible to observe motion information such as the wall thickness of almost the same segment myocardial. In addition, two-dimensional tracking in these C-mode images allows to expect a nearly three-dimensional tracking effect and can implement local myocardial wall motion analysis by pseudo three-dimensional tracking which shortens the computation time.

Fourth Embodiment

The fourth embodiment will be described next. This embodiment is a modification of the third embodiment, and uses the intersection position between each short-axis image and the myocardial on a long-axis image as a tracking target position concerning the long-axis image instead of the above annulus position.

Figure 16:
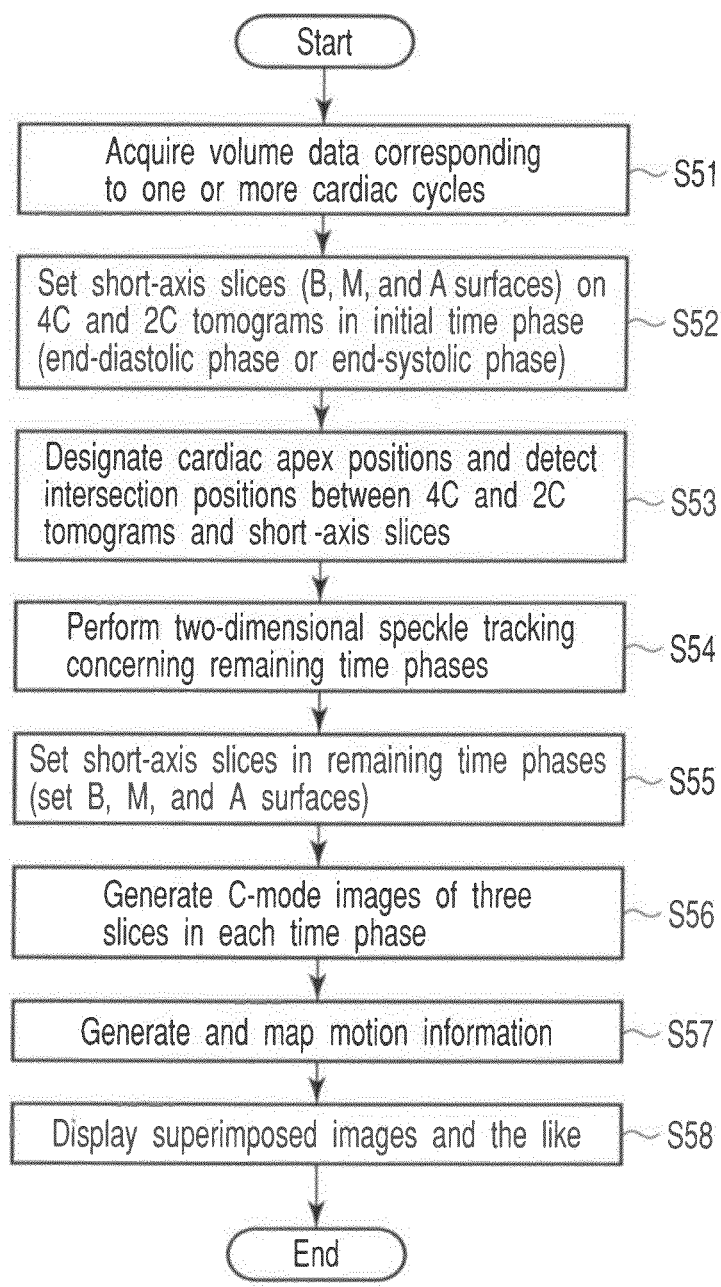
FIG. 16 is a flowchart showing a sequence of arbitrary slice tracking processing according to the fourth embodiment.

FIG. 16 is a flowchart showing a sequence of arbitrary slice tracking processing according to the fourth embodiment. The contents of processing in each step will be described below.

As shown in FIG. 16, first of all, the volume data of a heart as a diagnosis target concerning each of cardiac phases t0, t1, . . . , tn is acquired by volume scanning throughout a period T, and three long-axis tomograms are extracted from two long-axis slices comprising 4C and 2C images (or a combination of 4C and 3C images or all 4C, 2C, and 3C images) (step S51).

Based on an instruction from an operation unit 41, an initial time phase (preferably an end-diastolic phase or an end-systolic phase) from which tracking is started is designated, and the levels of short-axis slices (i.e., the levels of B, M, and A surfaces) are set on the long-axis tomograms in the initial time phase (step S52).

When the position of a cardiac apex portion in each time phase is designated, the intersection position between each short-axis slice and the myocardial in the initial time phase is detected by using a known edge detection technique (step S53). The position of an cardiac apex portion in each time phase is designated in the above manner.

Each intersection position on each short-axis slice is then tracked within each long-axis image concerning at least one cardiac cycle by performing tracking in the remaining time phases using the two-dimensional pattern matching technique (step S54). A tracking processing unit 33 sets C-mode image levels on the basis of the intersection position of each short-axis slice (step S55).

The image generating unit 21 reconstructs C-mode images concerning the set short-axis slices (step S56). C-mode images are reconstructed in the above manner.

Figure 17:
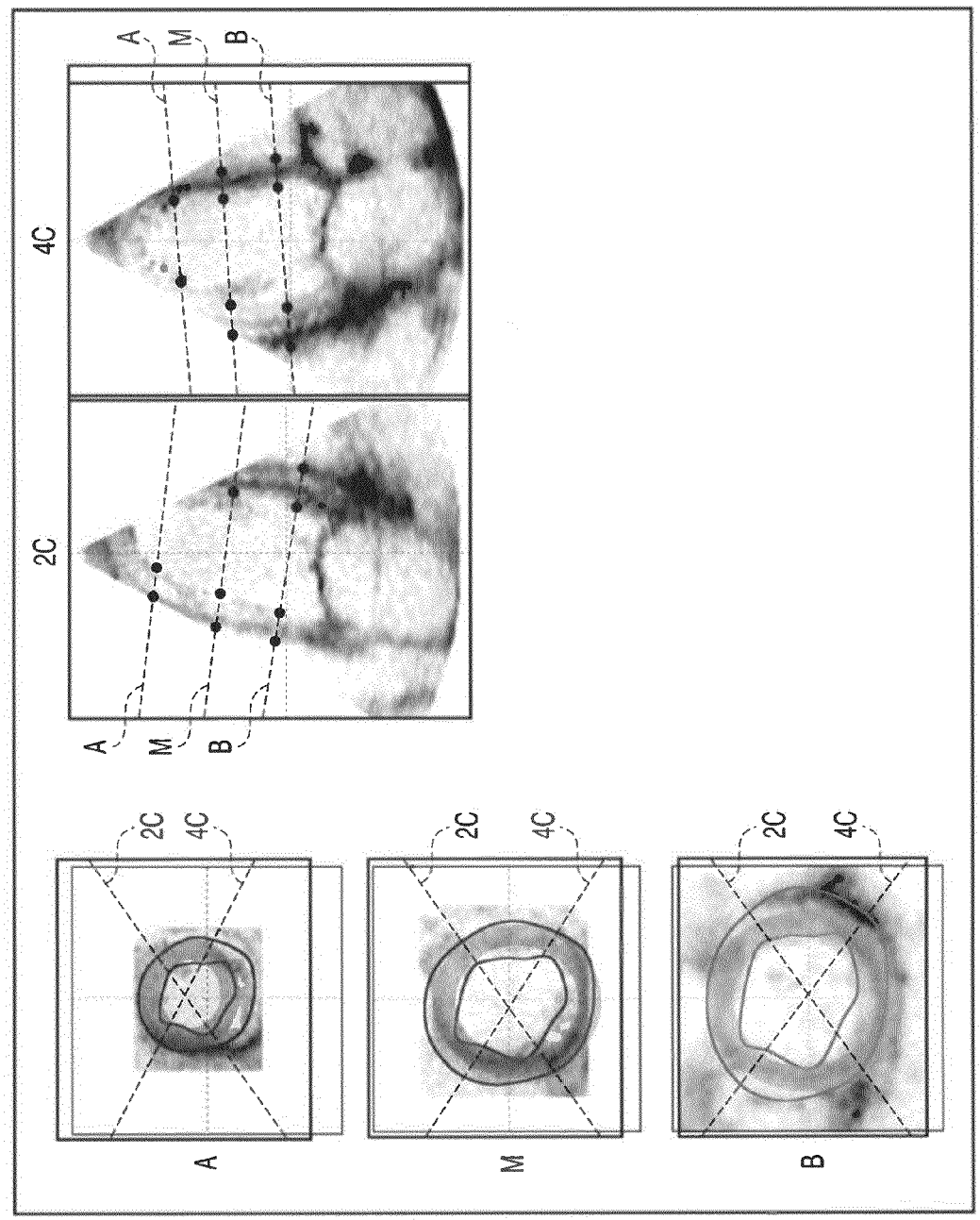
FIG. 17 is a view showing an example of the display form of motion information obtained by tracking processing according to the fourth embodiment.

Arbitrary myocardial wall motion parameters such as a radial-strain are computed by performing two-dimensional tracking in short-axis images tracked in the central axis direction in the above manner (step S57). The computed parameters are superimposed on the above C-mode images and displayed (step S58). FIG. 17 shows a preferred display example based on this embodiment.

With the above arrangement, the same effects as those of the third embodiment can be obtained.

Fifth Embodiment

The fifth embodiment will be described below. An apparatus according to this embodiment defines and computes first, in a three-dimensional space, myocardial wall motion information in the wall thickness direction (e.g., a physical quantity defined by using the three-dimensional distance between endo and epicardium, such as a radial strain, a radial strain rate, or a wall thickness), and superimposes/displays the information in color by projecting the information on arbitrary slices. This makes it possible to evaluate myocardial wall motion information in the wall thickness direction, which is accurately computed three-dimensionally, on two-dimensional tomograms with which the examiner has been familiar.

For a concrete description, assume that in this embodiment, a slice on which myocardial wall motion information in the wall thickness direction which is defined in the three-dimensional space is projected is an arbitrary slice temporally tracked and acquired by either of the techniques in the first to fourth embodiments. However, the technical idea of this embodiment is not limited to this. Assume that a slice set at a position where no temporal variation occurs is to be observed. In this case, even using slices acquired without using any of the techniques in the first to fourth embodiments allows to evaluate myocardial wall motion information in the wall thickness direction, which is accurately computed three-dimensionally, on two-dimensional tomograms.

[Computation of Motion Information]

A motion information computing unit 37 computes myocardial wall motion information in the wall thickness direction in each time phase in a three-dimensional space by using volume data concerning a tissue displacement in each time phase which is generated by a volume data generating unit 35 and an arbitrary slice in each time phase which is acquired by a tracking processing unit 33. That is, the motion information computing unit 37 specifies each position on an epicardium which corresponds to each position on an endocardium defined by an arbitrary slice set in each volume data (existing on the arbitrary slice) and computes motion information (myocardial wall motion information in the wall thickness direction) such as a wall thickness or radial strain rate.

Note that computation processing for myocardial wall motion information in the wall thickness direction is executed in, for example, step S5 in FIG. 2, step S35 in FIG. 11, step S47 in FIG. 4, and step S57 in FIG. 16.

[Image Display]

Figure 19:
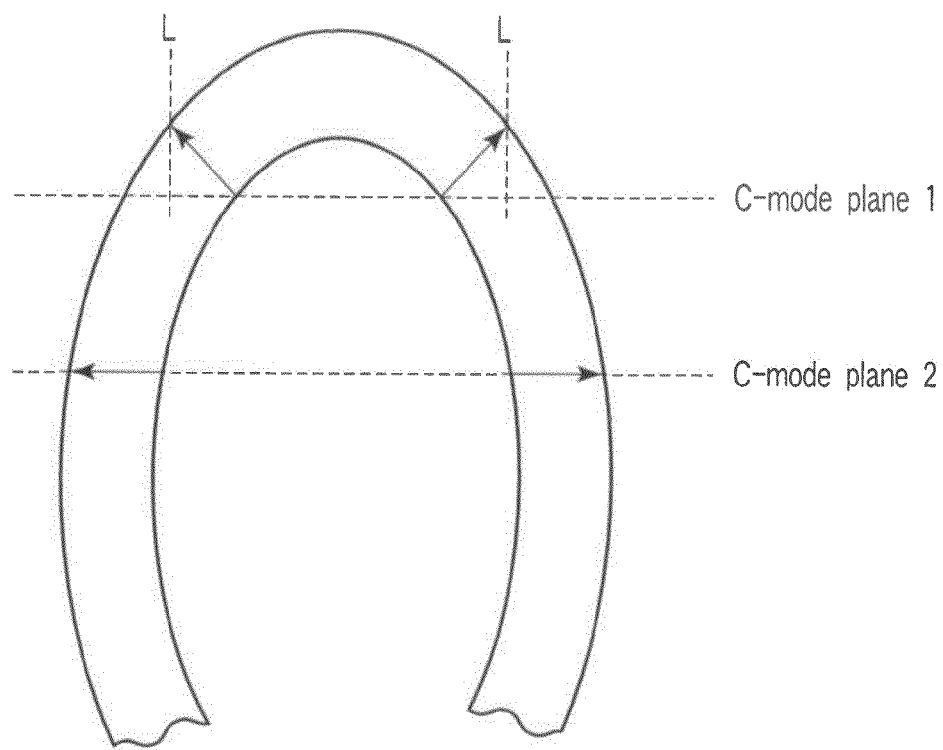
FIG. 19 is a view for explaining the projection of myocardial wall motion information in the wall thickness direction on a C-mode plane.

An image generating unit 21 then projects the computed myocardial wall motion information in the wall thickness direction in each time phase onto each projection surface. If, for example, the projection surfaces are C-mode plane 1 and C-mode plane 2 as shown in FIG. 19, the image generating unit 21 projects positions on the epicardium defined in a direction perpendicular to the long-axis direction (straight line L direction) with reference to positions on an endocardium onto corresponding position components on C-mode plane 1 and C-mode plane 2. A display unit 23 displays superimposed images obtained by superimposing the myocardial wall motion information in the wall thickness direction on C-mode images (monochrome images) in, for example, the form shown in FIG. 20.

Note that this image display processing is executed in, for example, step S6 in FIG. 2, step S36 in FIG. 11, step S48 in FIG. 14, and step S58 in FIG. 16.

Figure 20:
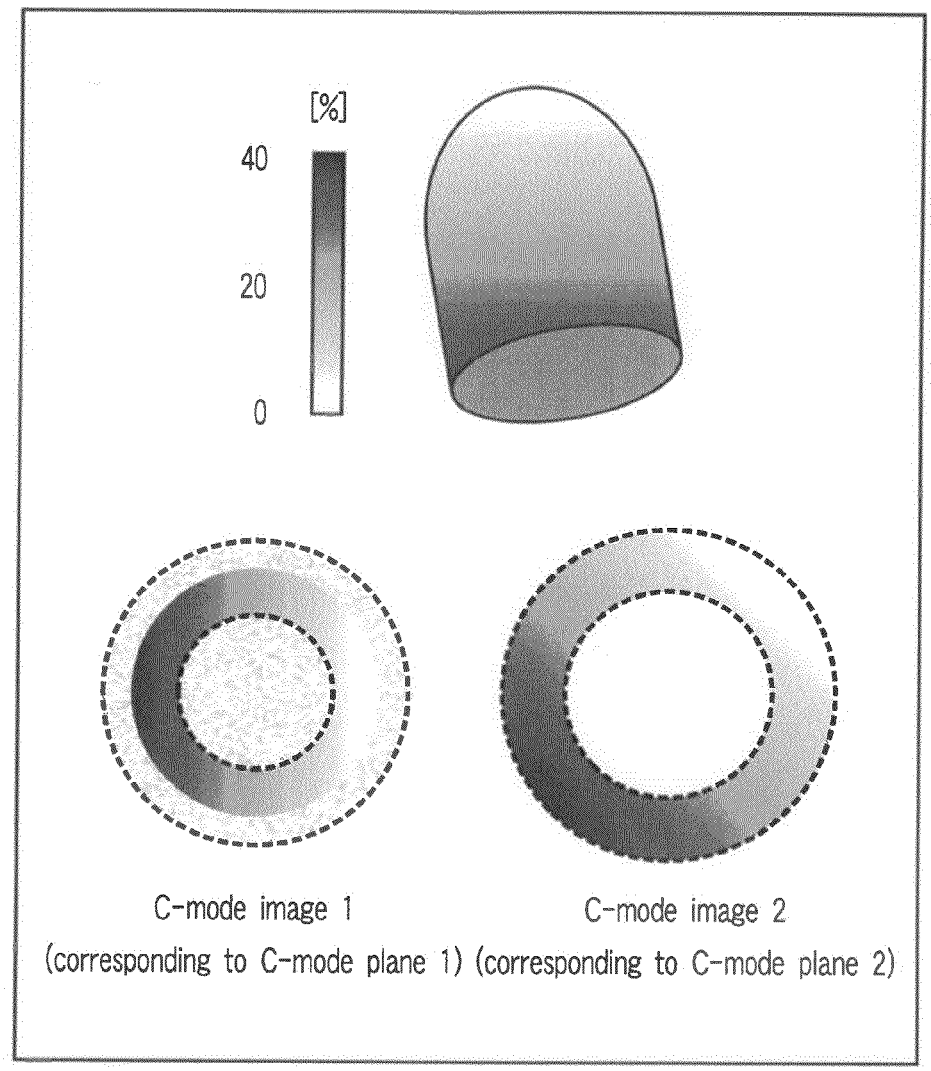
FIG. 20 is a view showing an example of the display form of a superimposed image obtained by projecting myocardial wall motion information in the wall thickness direction on a C-mode image.

The display form of myocardial wall motion information in the wall thickness direction shown in FIG. 20 accurately expresses the positional relationship between the area on which motion information is projected and cardiac wall area based on a C-mode image as shown in FIG. 19. In this display form, however, if an epicardium position on a projected C-mode image shifts from a projection position component of the epicardium (in the case of C-mode plane 1 in FIG. 19), the display area of the myocardial wall motion information in the wall thickness direction does not coincide with the cardiac wall area on the C-mode image. This gives the user an unnatural impression at the time of observation.

FIG. 21 shows another example of the display form of myocardial wall motion information in the wall thickness direction, which is designed not to give such an unnatural impression. In this display form, when images are superimposed and displayed, the size of the display area of myocardial wall motion information in the wall thickness direction is made to correspond to the size of the cardiac wall area on the C-mode image. This display form is an inaccurate expression from the viewpoint of the positional relationship between an area on which motion information is projected and a cardiac wall area based on a C-mode image, but can reduce the above unnatural impression given to the user. Note that the user can switch between the display form shown in FIG. 20 and the display form shown in FIG. 21 by, for example, predetermined operation using an operation unit 41 at an arbitrary timing.

According to the above arrangement, myocardial wall motion information in the wall thickness direction can be accurately computed three-dimensionally, and can be projected on a predetermined slice such as a C-mode plane. Therefore, the user can evaluate the accurate myocardial wall motion information in the wall thickness direction on a two-dimensional tomogram with which the user has been familiar.

A superimposed image obtained by superimposing myocardial wall motion information in the wall thickness direction on a C-mode image can be displayed while the size of the display area of the myocardial wall motion information in the wall thickness direction is made to correspond to the size of the cardiac wall area on the C-mode image. Even when the incoincidence between the display area of myocardial wall motion information in the wall thickness direction and the cardiac wall area on the C-mode image gives the user an unnatural impression, changing the display form can implement image observation with a natural impression.

The present invention is not limited to the above embodiments, and constituent elements can be modified and embodied in the execution stage within the spirit and scope of the invention. The following are concrete modifications.

(1) Each function according to the embodiments can also be implemented by installing programs for executing the corresponding processing in a computer such as a workstation and retrieving them in a memory. In this case, the programs which can cause the computer to execute the corresponding techniques can be distributed by being stored in recording media such as magnetic disks (floppy (registered trademark) disks, hard disks, and the like), optical disks (CD-ROMs, DVDs, and the like), and semiconductor memories.

Figure 18:
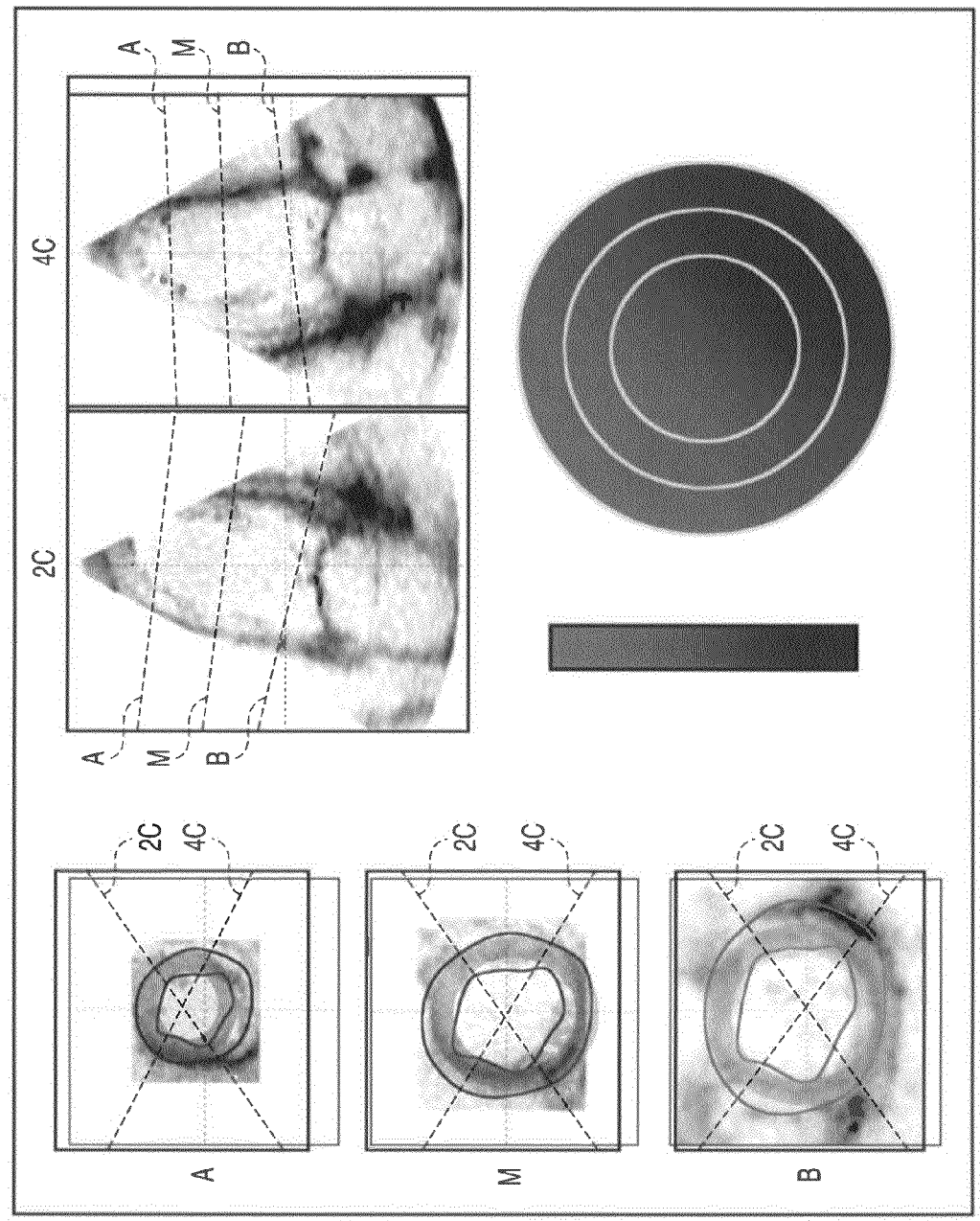
FIG. 18 is a view showing a modification of the display form of motion information obtained by tracking processing according to each embodiment.

(2) In each embodiment, motion information concerning an arbitrary slice acquired by arbitrary slice tracking processing can be displayed upon being coordinate-converted into a polar map, as shown in, for example, FIG. 18, instead of being projected/displayed on a predetermined MPR tomogram, or simultaneously with projection display. Referring to FIG. 18, the lower right display corresponds to polar map display. The polar map is displayed together with a color bar for color conversion of myocardial wall motion information. This makes it possible to grasp, with high visibility, how myocardial wall motion information in the entire left ventricle spreads, by using myocardial wall motion information accurately computed locally.

(3) Each embodiment described above has exemplified the case in which spatiotemporal distribution data concerning the movement vector of each tissue or the displacement of a tissue is acquired by the technique using speckle tracking. However, the present invention is not limited to this, and spatiotemporal distribution data can be generated on the basis of two-dimensional or three-dimensional image data concerning a plurality of time phases which are acquired by the tissue Doppler method.

In addition, various inventions can be made by proper combinations of a plurality of constituent elements disclosed in the above embodiments. For example, several constituent elements may be omitted from all the constituent elements disclosed in the above embodiments. Furthermore, constituent elements in different embodiments may be properly combined.

What is claimed is:

1. An ultrasonic image processing apparatus comprising:
a storage unit which stores volume data acquired for each time phase concerning periodic motion of an object to be examined which periodically moves by scanning the object with ultrasonic waves;
a setting unit which sets an arbitrary slice in volume data corresponding to a predetermined time phase;

a movement vector processing unit which determines a movement amount of the object between two different time phases;

a tracking unit which moves a plane corresponding to the arbitrary slice in said each volume data corresponding to remaining time phases concerning the periodic motion by executing tracking processing of tracking a temporal change in a position of the arbitrary slice in the predetermined time phase, in the tracking processing, a position of each slice being determined based on a plurality of motion vectors at points on a slice corresponding to a preceding time phase;

an image generating unit which generates a first ultrasonic image in said each time phase on the basis of data corresponding to the plane corresponding to the arbitrary slice in said each time phase; and a display unit which displays the first ultrasonic image for each time phase, wherein the tracking unit computes a movement vector concerning the plane corresponding to the arbitrary slice in the predetermined time phase, and executes the tracking processing by using the movement vector in the predetermined time phase and the arbitrary slice in the predetermined time phase.

2. An apparatus according to claim 1, wherein the tracking unit sets an area to which a plane corresponding to the arbitrary slice in an immediately preceding or succeeding time phase is moved by using the movement vector in the immediately preceding or succeeding time phase as a plane corresponding to the arbitrary slice in the time phase, for each of remaining time phases ti (where i is an integer satisfying 1≤i≤n and n is an integer satisfying n≥2) concerning the periodic motion when the predetermined time phase is represented by tj (i≠j), calculates a movement vector concerning the plane corresponding to the arbitrary slice in the time phase, and moves an arbitrary slice in an immediately preceding or succeeding time phase by using the arbitrary slice in the time phase and the movement vector concerning the arbitrary slice in the time phase.

3. An apparatus according to claim 1, wherein the tracking unit calculates a three-dimensional movement vector at each position on the arbitrary slice for each time phase, and calculates an average of projection components of a three-dimensional movement vector at said each position with respect to a normal line to the arbitrary slice as a movement vector concerning the arbitrary slice for each time phase.

4. An apparatus according to claim 1, wherein the tracking unit calculates a three-dimensional movement vector at each position on the arbitrary slice for each time phase, and calculates an average of a three-dimensional movement vector at said each position as a movement vector concerning a plane corresponding to the arbitrary slice for each time phase.

5. An apparatus according to claim 1, wherein the tracking unit calculates a three-dimensional movement vector at each position on the arbitrary slice in each time phase as a movement vector concerning a plane corresponding to the arbitrary slice in each time phase, and executes the tracking processing by moving each position on a plane corresponding to the arbitrary slice in each time phase by using a three-dimensional movement vector at each position in said each time phase.

6. An apparatus according to claim 1, wherein
the object is a heart,
a plane corresponding to an arbitrary slice in the predetermined time phase is a short-axis slice of the heart, and
the first ultrasonic image is a short-axis image of the heart.

7. An apparatus according to claim 1, wherein
the object is a heart,
a plane corresponding to an arbitrary slice in the predetermined time phase is a long-axis slice of the heart, and
the first ultrasonic image is a long-axis image of the heart.

8. An apparatus according to claim 1, wherein
the object is a heart,
the setting unit sets the arbitrary slice containing an annulus region in a long-axis slice of the heart in the volume data corresponding to the predetermined time phase,
the tracking unit sets annulus region positions in remaining time phases concerning the periodic motion in said each volume data corresponding to the remaining time phases by two-dimensional pattern matching using said each volume data corresponding to the remaining time phases and the annulus region in the predetermined time phase, and
the image generating unit generates at least one short-axis image in said each time phase as the first ultrasonic image on the basis of position information of an annulus region in said each set time phase.

9. An apparatus according to claim 1, wherein
the object is a heart,
the setting unit sets a tracking position corresponding to a short-axis slice in a long-axis slice of the heart in the volume data corresponding to the predetermined time phase,
the tracking unit sets a tracking position on the long-axis slice in each of remaining time phases concerning the periodic motion in said each volume data corresponding to the remaining time phases by using said each volume data corresponding to the remaining time phases and a tracking position on the long-axis slice in the predetermined time phase, and
the image generating unit generates at least one short-axis image in said each time phase as the first ultrasonic image on the basis of a tracking position on the long-axis slice in said each set time phase.

10. An apparatus according to claim 1, wherein the image generating unit generates at least one of a tissue form image and a motion information image as the first ultrasonic image.

11. An apparatus according to claim 1, wherein the image generating unit generates the first ultrasonic image by processing including rendering.

12. An apparatus according to claim 1, wherein
the image generating unit generates a second ultrasonic image different from the first ultrasonic image for each time phase by using the volume data, and
the display unit displays the second ultrasonic image together with a marker indicating a position of the first ultrasonic image.

13. An apparatus according to claim 12, wherein the display unit displays the second ultrasonic image together with markers indicating positions of said first ultrasonic images corresponding to different time phases.

14. An apparatus according to claim 12, wherein the display unit displays the first ultrasonic image together with a marker indicating a position of the second ultrasonic image.

15. An apparatus according to claim 14, wherein the display unit displays the first ultrasonic image together with markers indicating positions of said second ultrasonic images corresponding to different time phases.

16. An apparatus according to claim 1, wherein
the object is a heart, and
the image generating unit generates, as the first image, a motion information image by converting motion information of the object into polar coordinates with a cardiac apex portion being a pole on the basis of data corresponding to an arbitrary slice for said each time phase.

17. An apparatus according to claim 1, wherein
the object is a heart,
the image generating unit computes motion information in a wall thickness direction of the heart by using the arbitrary slice, a plane corresponding to the arbitrary slice, and said plurality of volume data, and generates a third ultrasonic image in each time phase by projecting motion information in a wall thickness direction of the heart onto the first ultrasonic image, and
the display unit displays the third ultrasonic image in a predetermined form.

18. An apparatus according to claim 17, wherein the display unit displays the third ultrasonic image in a form accurately expressing a positional relationship between a cardiac wall area on the first ultrasonic image and an area on which motion information in the wall thickness direction is projected.

19. An apparatus according to claim 17, wherein the display unit displays the third ultrasonic image in a form which makes a cardiac wall area on the first ultrasonic image coincide with an area on which local motion information is projected.

20. An ultrasonic image processing apparatus comprising:
a storage unit which stores volume data acquired in each time phase of a heart by scanning the heart with ultrasonic waves;
a computing unit which computes local movement information of the heart in each time phase by using the volume data;
a setting unit which sets an arbitrary slice in volume data in a predetermined time phase;
a movement vector processing unit which determines a movement amount of the heart between two different time phases;
a tracking unit which moves a plane corresponding to the arbitrary slice in said each volume data corresponding to remaining time phases concerning periodic motion of the heart by executing tracking processing of tracking a temporal change in a position of the arbitrary slice in the predetermined time phase, in the tracking processing, a position of each slice being determined based on a plurality of motion vectors at points on a slice corresponding to a preceding time phase;
an image generating unit which generates a first ultrasonic image in each time phase on the basis of tissue structure data corresponding to the arbitrary slice and a second ultrasonic image in each time phase by projecting the local movement information of the heart on the first ultrasonic image; and
a display unit which displays the second ultrasonic image in each time phase,
wherein the tracking unit computes a movement vector concerning the plane corresponding to the arbitrary slice in the predetermined time phase, and executes the tracking processing by using the movement vector in the predetermined time phase and the arbitrary slice in the predetermined time phase.

21. An apparatus according to claim 20, wherein the computing unit computes three-dimensional movement vector information; and
the image generating unit tracks the arbitrary slice in the volume data in each time phase by using the local movement information in each time phase and generates the second ultrasonic image in each time phase by using data corresponding to the arbitrary slice in the volume data.

22. An ultrasonic image processing method comprising:
setting an arbitrary slice in volume data corresponding to a predetermined time phase, the volume data being acquired for each time phase concerning periodic motion of an object to be examined which periodically moves by scanning the object with ultrasonic waves;
determining a movement amount of the object between two different time phases;
moving a plane corresponding to the arbitrary slice in said each volume data corresponding to remaining time phases concerning the periodic motion by executing tracking processing of tracking a temporal change in a position of the arbitrary slice in the predetermined time phase, in the tracking processing, a position of each slice being determined based on a plurality of motion vectors at points on a slice corresponding to a preceding time phase;
generating a first ultrasonic image in said each time phase on the basis of data corresponding to the plane corresponding to the arbitrary slice in said each time phase; and
displaying the first ultrasonic image for each time phase,
wherein the tracking processing comprises computing a movement vector concerning the plane corresponding to the arbitrary slice in the predetermined time phase, and using the movement vector in the predetermined time phase and the arbitrary slice in the predetermined time phase.

23. An ultrasonic image processing method comprising:
computing local movement information of a heart in each time phase by using volume data acquired in each time phase of the heart by scanning the heart with ultrasonic waves;
setting an arbitrary slice in volume data;
moving a plane corresponding to the arbitrary slice in said each volume data corresponding to remaining time phases concerning periodic motion of the heart by executing tracking processing of tracking a temporal change in a position of the arbitrary slice in a predetermined time phase, in the tracking processing, a position of each slice being determined based on a plurality of motion vectors at points on a slice corresponding to a preceding time phase;
generating a first ultrasonic image in each time phase on the basis of tissue structure data corresponding to the arbitrary slice and a second ultrasonic image in each time phase by projecting the local movement information of the heart on the first ultrasonic image; and
displaying the second ultrasonic image in each time phase
wherein the tracking processing comprises computing a movement vector concerning the plane corresponding to the arbitrary slice in the predetermined time phase, and using the movement vector in the predetermined time phase and the arbitrary slice in the predetermined time phase.

* * * * *

UNITED STATES PATENT AND TRADEMARK OFFICE
CERTIFICATE OF CORRECTION

| | |
|---|---|
| PATENT NO. | : 8,565,504 B2 |
| APPLICATION NO. | : 12/109805 |
| DATED | : October 22, 2013 |
| INVENTOR(S) | : Yasuhiko Abe et al. |

It is certified that error appears in the above-identified patent and that said Letters Patent is hereby corrected as shown below:

On the title page, Item (73), the Assignees' Information is incorrect. Item (73) should read:

--(73) Assignees: Kabushiki Kaisha Toshiba, Tokyo (JP);
Toshiba Medical Systems Corporation, Otawara-shi (JP)--

Signed and Sealed this
Twenty-eighth Day of January, 2014

Michelle K. Lee
*Deputy Director of the United States Patent and Trademark Office*